United States Patent [19]

Hayashi et al.

[11] Patent Number: 5,116,858
[45] Date of Patent: May 26, 1992

[54] 4-IMIDAZOLINE DERIVATIVES

[75] Inventors: Yoshio Hayashi, Ushiku; Yasuhiro Morinaka, Tsuchiura; Masaki Shinoda, Yokohama; Hiroyoshi Nishi, Ibaraki; Kazutoshi Watanabe; Nobuko Fukushima, both of Yokohama, all of Japan

[73] Assignee: Mitsubishi Kasei Corporation, Tokyo, Japan

[21] Appl. No.: 514,832

[22] Filed: Apr. 26, 1990

[30] Foreign Application Priority Data

Apr. 26, 1989 [JP] Japan .................. 1-107028

[51] Int. Cl.⁵ .................. C07D 233/70; A61K 31/415
[52] U.S. Cl. .................. 514/391; 548/321; 548/322
[58] Field of Search .......... 548/300, 317, 322, 321; 514/391

[56] References Cited

U.S. PATENT DOCUMENTS

| | | | |
|---|---|---|---|
| 3,629,279 | 12/1971 | Pesterfield | 548/322 |
| 4,349,684 | 9/1981 | Lautenschlager et al. | 548/320 |
| 4,460,598 | 7/1984 | Lautenschlager | 548/337 |
| 4,957,941 | 9/1990 | Davis | 548/300 |

FOREIGN PATENT DOCUMENTS 0104342  4/1984  European Pat. Off. .

Primary Examiner—Robert Gerstl
Attorney, Agent, or Firm—Wenderoth, Lind & Ponack

[57] ABSTRACT

4-Imidazoline derivatives represented by the formula (I) and/or formula (II):

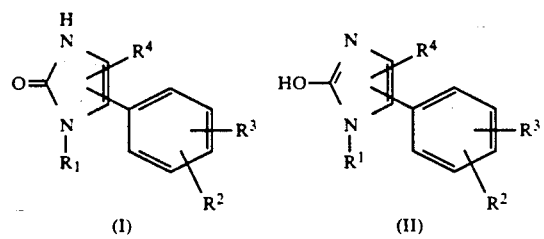

wherein $R^1$ represents $C_1$–$C_6$ alkyl, $C_3$–$_8$ alkenyl, $C_3$–$C_6$ alkynyl, $C_3$–$C_6$ cycloalkyl, or optionally substituted aralkyl; $R^2$ and $R^3$ independently represent hydrogen, $C_3$–$C_{20}$ alkyl, $C_3$–$C_{20}$ alkenyl, $C_3$–$C_{20}$ alkynyl, $C_3$–$C_{20}$ alkoxy, $C_3$–$C_{20}$ alkenyloxy, $C_3$–$C_{20}$ alkynyloxy, $C_3$–$C_6$ cyloalkyl, $C_1$–$C_{10}$ alkylthio, or optionally substituted aralkyl or aralkyloxy; $R^4$ represents $C_1$–$C_6$ alkyl, $C_3$–$C_8$ cycloalkyl, or optionally substituted aralkyl; provided that $R^2$ and $R^3$ cannot be hydrogen at the same time, and pharmaceutically acceptable salts thereof. A pharmaceutical formulation containing the compound is also provided.

7 Claims, No Drawings

4-IMIDAZOLINE DERIVATIVES

The present invention relates to novel 4-imidazoline compounds which exhibit inhibitory activity against cytotoxicities caused by active oxygen species, and which possess memory-improving action partly attributable to said inhibitory activity.

With the advent of a highly civilized yet aging society, ischemic diseases such as cerebral ischemia, ischemic heart disease, and ischemic nephropathy have become major causes of death in developed countries. It has become apparent that the active oxygen species, such as superoxide anion radical, hydroxy radical, singlet-state oxygen, and peroxidized lipids, are largely responsible for the generation and development of the diseases. Such changes will occur not only during ischemia, but also further will be accelerated and advanced by reoxidation through the blood reflow after the ischemia.

Extensive research over the last few years has revealed that the active oxygen species are also associated with ischemic disorders of the small intestine, atherosclerosis, oxygen-poisoned lungs (acute lung injury), abnormal neutrophil phagocytosis, and the like ["Noshinkei", 41, 157-163 (1989)]; and possibly may be associated with dementia of Alzheimer's type ["Nippon Rinsho", 46, 1616 (1988); "Seishinyakuryo Kikin Kenkyu Nenpo", 19, 28 (1988)]. It has been also reported that pathergasia, such as cognitive dysfunction or memory impairment, is caused by active oxygen species inhibiting the uptake of gamma aminobutyric acid (GABA), which is an inhibitory neurotransmitter found in central nervous system (CNS), whereby binding of GABA to its receptor is accelerated, which causes functional deterioration of neurons in CNS [Brain Research, 333, 111 (1985); Journal of Neurochemistry, 47, 1804 (1986)].

Specific examples of pathologies, which are associated with active oxygen species and can presumably be treated with radical scavengers as mentioned below, are sepsis, asthma, bronchitis, endotoxin shock, gastrointestinal ulcer, hepatitis, pancreatitis, diabetic cataract, inflammation, arthritis, dermatitis, and organ transplantation (Y. Oyanagi, SOD and active oxygen modulators - Pharmacology and clinical trials, Nihon-Igakukan, Tokyo, 1989).

As can be seen from the above, inhibition of active oxygen species which directly or indirectly causes several pathogenesies as mentioned above will serve as a prophylactic or therapeutic treatment of the pathologies, because such inhibition will protect living cells from functional deterioration or degenerations.

A variety of radical scavengers and lipid-peroxidation inhibitors have been proposed as an inhibitory agent for cytotoxicities caused by active oxygen species. Examples of such inhibitory agents are Vitamin C, Vitamin E, idebenone having the following formula [Biochemical and Biophysical Research Communications, 125 1046 (1984); "Takeda Kenkyusho-ho", 44, 30 (1985)]:

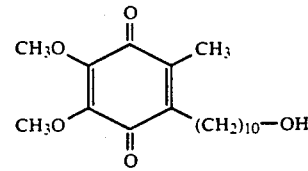

nizofenone of the following formula [Journal of Neurochemistry, 37, 934 (1981)]:

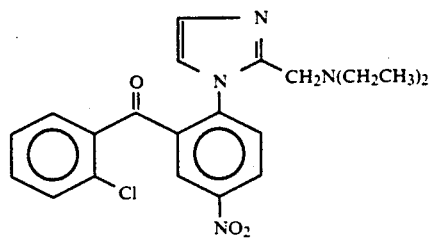

CV-3611 of the following formula [Journal of Medicinal Chemistry, 31 793 (1988)]:

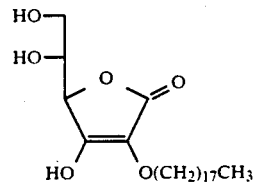

E-2001 of the following formula [The Japanese Journal of Pharmacology, 46, Supplementum 245p, (1988)]:

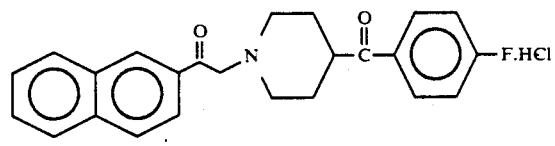

and ergot alkaloid dihydroergotoxine, and the like.

The above-mentioned compounds, however, are all unsatisfactory as inhibitory agents for cytotoxicities because Vitamin C and Vitamin E are very limited in their activities, and with idebenone, nizofenone, CV-3611, and E-2001, there is a disadvantage in that the production of these compounds requires many synthetic steps. With nizofenone, there is an additional drawback in that it possesses a strong inhibitory action on CNS ["Iyakuhin Kenkyu", 16, 1 (1985)].

On the other hand, a variety of 4-imidazolin-2-one derivatives, which are structurally similar to compounds of the present invention, are known. For example, a compound of the following formula is described in Journal of Heterocyclic Chemistry, 16, (5), 983, (1979):

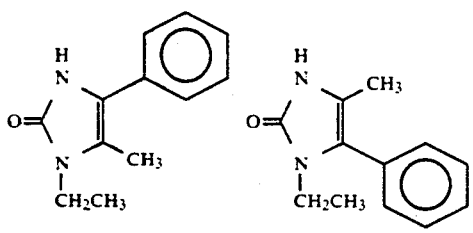
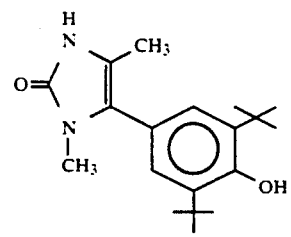

U.S. Pat. No. 3,721,738 discloses a compound of the formula:

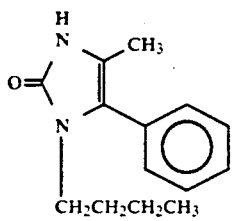

and the use of the compound as an antithrombotic and antiatherosclerotic agent.

DE 3,504,677 discloses an intermediate for preparing a compound having antithrombotic, antiatherosclerotic, lipid lowering, and antiinflammatory actions, which intermediate is represented by the formula:

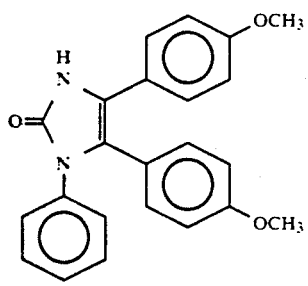

U.S. Pat. No. 3,629,279 discloses, among others, a compound having an antiinflammatory activity, which is shown by the formula:

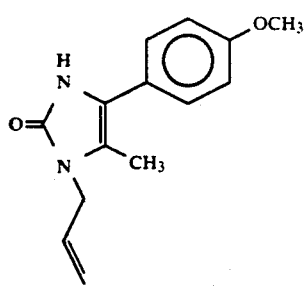

None of the above-listed literature indicates that the foregoing compounds are useful as a lipo-peroxidation inhibitor, a radical scavenger, or a memory-improving agent. In fact, they exhibit very limited lipoperoxidation-inhibitory activity as shown in the Examples following.

European Patent No. 0,059,090 discloses a compound having the following formula:

and it shows that the compound is useful as an antirheumatic, antiinflammatory, analgetic, or antiallergic agent, as well as a lipoxygenase-inhibitor or a radical scavenger. However, the European patent teaches nothing about lipoperoxidation-inhibitory action or memory-improving action of the compound. In addition, the above compound is structurally distinct from any one of the compounds of the present invention in that the former bears 3,5-di-t-butyl-4-hydroxyphenyl moiety.

We have now discovered a class of compounds which exhibit strong lipoperoxidation-inhibitory action and which are useful as a memory-improving agent at lower dosage. The compounds of the present invention are 4-imidazolin-2-one derivatives and their enol-type tautomer, i.e., 2-hydroxy-4-imidazole derivatives, having the following formulae (I) and (II) respectively:

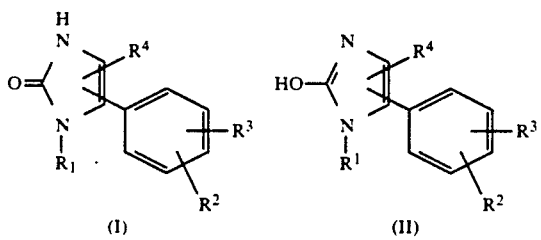

wherein $R^1$ represents $C_1$-$C_8$ alkyl, $C_3$-$C_8$ alkenyl, $C_3$-$C_8$ alkynyl, $C_3$-$C_8$ cycloalkyl, or a group of the formula:

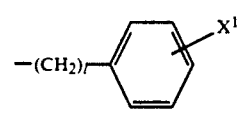

wherein $X^1$ is hydrogen, halogen, $C_1$-$C_3$ alkyl, or $C_1$-$C_3$ alkoxy, and l is an integer of 0-3; $R^2$ and $R^3$ independently represent hydrogen, $C_3$-$C_{20}$ alkyl, $C_3$-$C_{20}$ alkenyl, $C_3$-$C_{20}$ alkynyl, $C_3$-$C_{20}$ alkoxy, $C_3$-$C_{20}$ alkenyloxy, $C_3$-$C_{20}$ alkynyloxy, $C_3$-$C_8$ cycloalkyl, $C_1$-$C_{10}$ alkylthio, a group of the formula:

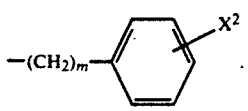

wherein $X^2$ is hydrogen, halogen, $C_1$-$C_3$ alkyl, or $C_1$-$C_3$ alkoxy, and m is an integer of 0-3, or a group of the formula:

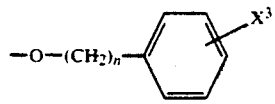

wherein $X^3$ is hydrogen, halogen, $C_1$-$C_3$ alkyl, or $C_1$-$C_3$ alkoxy, and n is an integer of 0–3; $R^4$ represents $C_1$-$C_6$ alkyl, $C_3$-$C_8$ cycloalkyl, or a group of the formula:

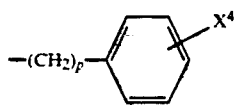

wherein $X^4$ is hydrogen, halogen, $C_1$-$C_3$ alkyl, or $C_1$-$C_3$ alkoxy, and p is an integer of 1–3; provided that $R^2$ and $R^3$ cannot be hydrogen at the same time, and pharmaceutically acceptable salts thereof.

As stated above, the compound represented by the formula (II) is a tautomer of the compound of the formula (I), and both compounds are included in the present invention. However, for the purpose of simplicity, only the compound of the formula (I) is referred to in the following description unless reference to the tautomeric compound (II) is inevitable.

Specific examples of $R^1$ include $C_1$-$C_8$ alkyl such as methyl, ethyl, propyl, hexyl, and octyl; $C_3$-$C_8$ alkenyl such as propenyl, butenyl, pentenyl, and octenyl; $C_3$-$C_8$ alkynyl such as propynyl, butynyl, heptynyl, and octynyl; $C_3$-$C_8$ cycloalkyl such as cyclopropyl, cyclopentyl, cyclohexyl, and cyclooctyl; phenyl; halogen-substituted phenyl such as chlorophenyl and fluorophenyl; $C_1$-$C_3$ alkyl-substituted phenyl such as tolyl and cumenyl; $C_1$-$C_3$ alkoxy-substituted phenyl such as methoxyphenyl and propoxyphenyl; benzyl; halogen-substituted benzyl such as chlorobenzyl and bromobenzyl; $C_1$-$C_3$ alkyl-substituted benzyl such as methylbenzyl and propylbenzyl; $C_1$-$C_3$ alkoxy-substituted benzyl such as anisyl and propoxybenzyl; phenethyl; halogen-substituted phenethyl such as chlorophenethyl and iodophenethyl; $C_1$-$C_3$ alkyl-substituted phenethyl such as methylphenethyl and propylphenethyl; $C_1$-$C_3$ alkoxyphenethyl such as methoxyphenethyl and propoxyphenethyl; 3-phenylpropyl; halogen-substituted 3-phenylpropyl such as 3-(chlorophenyl)-propyl and 3-(fluorophenyl)propyl; $C_1$-$C_3$ alkyl-substituted 3-phenylpropyl such as 3-(methylphenyl)propyl and 3-(propylphenyl)propyl; and $C_1$-$C_3$ alkoxy-substituted 3-phenylpropyl such as 3-(methoxyphenyl)propyl and 3-(propoxyphenyl)propyl.

Specific examples of $R^2$ and $R^3$ are each hydrogen; $C_3$-$C_{20}$ alkyl such as propyl, butyl, pentyl, decyl, octadecyl, and eicocyl; $C_3$-$C_{20}$ alkenyl such as propenyl, heptenyl, undecenyl, dodecenyl, heptadecenyl, and eicocenyl; $C_3$-$C_{20}$ alkynyl such as propynyl, octynyl, tetradecynyl, octadecynyl, and eicocynyl; $C_3$-$C_{20}$ alkoxy such as propoxy, hexyloxy, tridecyloxy, hexadecyloxy, and eicocyloxy; $C_3$-$C_{20}$ alkenyloxy such as propenyloxy, hexadecenyloxy, and eicocenyloxy; $C_3$-$C_{20}$ alkynyloxy such as propynyloxy, heptynyloxy, pentadecynyloxy, nonadecynyloxy, and eicocynyloxy; $C_3$-$C_8$ cycloalkyl such as hereinbefore described as specific examples of $R^1$; $C_1$-$C_{10}$ alkylthio such as methylthio, ethylthio, butylthio, heptylthio, nonylthio, and decylthio; phenyl, benzyl, phenethyl, and 3-phenylpropyl each optionally substituted by halogen, $C_1$-$C_3$ alkyl or $C_1$-$C_3$ alkoxy, such as those hereinbefore illustrated as specific examples of $R^1$; phenoxy; halogen-substituted phenoxy such as chlorophenoxy and fluorophenoxy; $C_1$-$C_3$ alkyl-substituted phenoxy such as methylphenoxy and propylphenoxy; $C_1$-$C_3$ alkoxy-substituted phenoxy such as methoxyphenoxy and propoxyphenoxy; benzyloxy; halogen-substituted benzyloxy such as chlorobenzyloxy and bromobenzyloxy; $C_1$-$C_3$ alkyl-substituted benzyloxy such as methylbenzyloxy and propylbenzyloxy; $C_1$-$C_3$ alkoxy-substituted benzyloxy such as methoxybenzyloxy and propoxybenzyloxy; phenethyloxy; halogen-substituted phenethyloxy such as chlorophenethyloxy and iodophenethyloxy; $C_1$-$C_3$ alkyl-substituted phenethyloxy such as methylphenethyloxy and propylphenethyloxy; $C_1$-$C_3$ alkoxy-substituted phenethyloxy such as methoxyphenethyloxy and propoxyphenethyloxy; 3-phenylpropoxy; halogen-substituted 3-phenylpropoxy such as 3-(chlorophenyl)propoxy and 3-(fluorophenyl)propoxy; $C_1$-$C_3$ alkyl-substituted 3-phenylpropoxy such as 3-(methylphenyl)propoxy and 3-(propylphenyl)propoxy; and $C_1$-$C_3$ alkoxy-substituted 3-phenylpropoxy such as 3-(methoxyphenyl)propoxy and 3-(propoxyphenyl)propoxy. As noted in the foregoing, $R^3$ and $R^4$ cannot represent hydrogen simultaneously.

$R^4$ specifically represents $C_1$-$C_6$ alkyl such as methyl, ethyl, propyl, butyl, pentyl and hexyl; $C_3$-$C_8$ cycloalkyl such as those illustrated hereinabove in the definition of $R^1$; and benzyl, phenethyl, and 3-phenylpropyl each optionally substituted by halogen, $C_1$-$C_3$ alkyl, or $C_1$-$C_3$ alkoxy, as specifically illustrated in the definition of $R^1$.

Preferred substituents represented by $R^1$ include $C_1$-$C_4$ alkyl such as methyl, ethyl, propyl, isopropyl, butyl, isobutyl, sec-butyl, and t-butyl; $C_5$-$C_6$ cycloalkyl such as cyclopentyl and cyclohexyl; phenyl optionally substituted by halogen, $C_1$-$C_3$ alkyl, or $C_1$-$C_3$ alkoxy; and arylalkyl, such as benzyl, phenethyl and 3-phenylpropyl, optionally substituted by halogen, $C_1$-$C_3$ alkyl, or $C_1$-$C_3$ alkoxy.

A preferred combination of $R^2$ and $R^3$ is obtained when $R^3$ represents hydrogen and $R^2$ represents $C_3$-$C_{20}$ alkyl; $C_3$-$C_{20}$ alkoxy; $C_5$-$C_6$ cycloalkyl; $C_1$-$C_5$ alkylthio such as methylthio, ethylthio, propylthio, butylthio, and pentylthio; phenyl; and arylalkyloxy such as phenoxy, benzyloxy, phenethyloxy, and 3-phenylpropoxy, each optionally substituted on their benzene ring by halogen, $C_1$-$C_3$ alkyl, or $C_1$-$C_3$ alkoxy. Especially preferred combination of $R^2$ and $R^3$ is obtained when $R^2$ locates at para-position.

Preferred substituents for $R^4$ include, similar to those for $R^1$, $C_1$-$C_4$ alkyl; $C_5$-$C_6$ cycloalkyl; arylalkyl such as benzyl, phenethyl, and 3-phenylpropyl, each optionally substituted on their benzene ring with halogen, $C_1$-$C_3$ alkyl, or $C_1$-$C_3$ alkoxy.

Pharmaceutically acceptable salts of the compounds of the present invention includes those formed between the compound (I) and an alkali metal such as sodium or potassium; an alkaline earth metal such as magnesium or calcium.

Specific examples of 4-imidazolin-2-one derivatives (I) and 2-hydroxy-4-imidazole derivatives (II) of the present invention are illustrated in the following Tables I, II and III. In the tables, the symbols "o", "m", and "p" respectively mean ortho, metha, and para position of a substituent on the associated benzene ring attached to the 4-imidazole ring.

TABLE 1

[Structure: imidazolinone with R³/R² on phenyl, R⁴ on C=C, R¹ on N]

| Compound No. | R¹ | R² | R³ | R⁴ | m.p. (°C.) |
|---|---|---|---|---|---|
| 1 | —CH₃ | p-(CH₂)₅CH₃ | —H | —CH₃ | 122–123 |
| 2 | —CH₃ | p-(CH₂)₃CH₃ | —H | —CH₃ | 180–180.5 |
| 3 | —CH₃ | p-(CH₂)₃CH₃ | —H | —CH₂CH₃ | 147–148 |
| 4 | —CH₃ | p-(CH₂)₃CH₃ | —H | cyclohexyl | 154–156 |
| 5 | —CH₃ | p-CH₂CH(CH₃)₂ | —H | —CH₃ | 195 |
| 6 | —CH₃ | p-(CH₂)₄CH₃ | —H | —CH₃ | 159 |
| 7 | —CH₃ | p-CH₂CH₂CH₃ | —H | —CH₃ | 141–143 |
| 8 | —CH₃ | p-cyclohexyl | —H | —CH₃ | 259–260 |
| 9 | —CH₃ | p-C(CH₃)₃ | —H | —CH₃ | 243–244 |
| 10 | —CH₃ | p-(CH₂)₆CH₃ | —H | —CH₃ | 116 |
| 11 | —CH₃ | p-(CH₂)₇CH₃ | —H | —CH₃ | 113–113.8 |
| 12 | —CH₃ | p-(CH₂)₉CH₃ | —H | —CH₃ | 95.5 |
| 13 | —CH₃ | p-(CH₂)₁₁CH₃ | —H | —CH₃ | 93.5–95 |
| 14 | —CH₃ | p-(CH₂)₁₃CH₃ | —H | —CH₃ | 90 |
| 15 | —CH₃ | p-(CH₂)₁₇CH₃ | —H | —CH₃ | 96 |
| 16 | —CH₃ | p-phenyl | —H | —CH₃ | 245 |
| 17 | —CH₃ | p-OCH(CH₃)₂ | —H | —CH₃ | 179–181 |
| 18 | —CH₃ | p-O(CH₂)₃CH₃ | —H | —CH₃ | 126–127 |
| 19 | —CH₃ | p-O(CH₂)₄CH₃ | —H | —CH₃ | 124–126 |
| 20 | —CH₃ | p-O(CH₂)₂CH(CH₃)₂ | —H | —CH₃ | 144–146 |
| 21 | —CH₃ | p-O(CH₂)₅CH₃ | —H | —CH₃ | 163–164 |
| 22 | —CH₃ | p-O(CH₂)₆CH₃ | —H | —CH₃ | 120–122 |

TABLE 1-continued

[Structure: phenyl ring with R¹ and R² substituents, connected to C(R⁴)=C(CH₃) group bonded to an imidazolinone ring (HN–C(=O)–N–R³)]

| Compound No. | R¹ | R² | R³ | R⁴ | m.p. (°C.) |
|---|---|---|---|---|---|
| 23 | —CH₃ | p-O(CH₂)₇CH₃ | —H | —CH₃ | 112.5–114 |
| 24 | —CH₃ | p-O(CH₂)₈CH₃ | —H | —CH₃ | 93 |
| 25 | —CH₃ | p-O(CH₂)₉CH₃ | —H | —CH₃ | 93–94 |
| 26 | —CH₃ | p-O(CH₂)₁₁CH₃ | —H | —CH₃ | 94–95 |
| 27 | —CH₃ | p-O(CH₂)₁₇CH₃ | —H | —CH₃ | 105–106 |
| 28 | —CH₃ | p-O-C₆H₅ | —H | —CH₃ | 197 |
| 29 | —CH₃ | p-OCH₂-C₆H₅ | —H | —CH₃ | 239 |
| 30 | —CH₃ | p-O(CH₂)₃-C₆H₅ | —H | —CH₃ | 167–168 |
| 31 | —CH₃ | p-SCH₃ | —H | —CH₃ | 189–190 |
| 32 | —CH₃ | p-S(CH₂)₃CH₃ | —H | —CH₃ | 140–141 |
| 33 | —CH₃ | o-O(CH₂)₃CH₃ | p-O(CH₂)₃CH₃ | —CH₃ | 160–161 |
| 34 | —CH₃ | p-CH₂CH₂CH₃ | —H | —CH₂CH₂CH₃ | |
| 35 | —CH₃ | p-CH₂CH₂CH₃ | —H | —CH₂-C₆H₅ | |
| 36 | —CH₃ | p-CH₂CH₂CH₃ | —H | —(CH₂)₃-C₆H₅ | |

TABLE 1-continued
Structure:
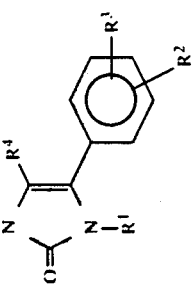
| Compound No. | R$^1$ | R$^2$ | R$^3$ | R$^4$ | m.p. (°C.) |
|---|---|---|---|---|---|
| 37 | —CH$_3$ | p-CH$_2$CH$_2$CH$_3$ | —H | —CH$_2$—C$_6$H$_4$—CH$_3$ (p) | |
| 38 | —CH$_3$ | p-CH$_2$CH$_2$CH$_3$ | —H | —CH$_2$—C$_6$H$_4$—OCH$_3$ (p) | |
| 39 | —CH$_3$ | p-CH$_2$CH$_2$CH$_3$ | —H | —CH$_2$—C$_6$H$_4$—Cl (p) | |
| 40 | —CH$_3$ | p-CH$_2$CH$_2$CH$_3$ | o-(CH$_2$)$_3$CH$_3$ | —CH$_3$ | |
| 41 | —CH$_3$ | p-cyclohexyl | —H | —CH$_2$CH$_3$ | |
| 42 | —CH$_3$ | p-cyclohexyl | —H | —CH(CH$_3$)$_2$ | |
| 43 | —CH$_3$ | p-cyclohexyl | —H | —C(CH$_3$)$_3$ | |

TABLE 1-continued

| Compound No. | R¹ | R² | R³ | R⁴ | m.p. (°C.) |
|---|---|---|---|---|---|
| 44 | —CH₃ | p-(phenyl) | —H | —CH₂CH₃ | |
| 45 | —CH₃ | o-(CH₂)₃CH₃ | —H | —CH₃ | |
| 46 | —CH₃ | p-(CH₂)(phenyl) | —H | —CH₃ | |
| 47 | —CH₃ | p-O(phenyl) | —H | —C(CH₃)₃ | |
| 48 | —CH₃ | p-O(CH₂)₉CH₃ | —H | —(CH₂)₄CH₃ | |
| 49 | —CH₃ | p-S(CH₂)₇CH₃ | —H | —CH₂CH₃ | |
| 50 | —CH₃ | p-S(CH₂)₅CH₃ | —H | —CH₂CH₃ | |
| 51 | —CH₃ | p-(CH₂)₉CH₃ | —H | —(CH₂)₅CH₃ | |
| 52 | —CH₃ | p-(CH₂)₂(3-Cl-phenyl) | —H | —CH₃ | |
| 53 | —CH₃ | p-(CH₂)₃(4-F-phenyl) | —H | cyclohexyl | |
| 54 | —CH₂CH₃ | p-CH₂CH₂CH₃ | —H | —CH₃ | 127-128 |
| 55 | —CH₂CH₃ | p-(CH₂)₃CH₃ | —H | —CH₃ | 132-133 |

TABLE 1-continued

Structure:

$$\begin{array}{c} R^4 \quad R^3 \\ \diagdown \quad \diagup \\ C=C-\text{Ar}(R^2,R^3) \\ | \quad | \\ HN \quad N-R^1 \\ \diagdown \diagup \\ C \\ \| \\ O \end{array}$$

| Compound No. | R¹ | R² | R³ | R⁴ | m.p. (°C.) |
|---|---|---|---|---|---|
| 56 | —CH₂CH₃ | p-(CH₂)₃CH₃ | —H | —CH₂CH₃ | 117–118 |
| 57 | —CH₂CH₃ | p-(CH₂)₃CH₃ | —H | cyclohexyl | 144–146 |
| 58 | —CH₂CH₃ | p-O(CH₂)₃CH₃ | —H | —CH₃ | 139–141 |
| 59 | —CH₂CH₃ | p-O(CH₂)₇CH₃ | —H | —CH₃ | 108–110 |
| 60 | —CH₂CH₃ | p-OCH(CH₃)₂ | —H | —CH₃ | 202–203 |
| 61 | —CH₂CH₃ | p-S(CH₂)₃CH₃ | —H | —CH₃ | 106.5–109 |
| 62 | —CH₂CH₃ | m-(CH₂)₃CH₃ | —H | —CH₃ | |
| 63 | —CH₂CH₃ | o-(CH₂)₃CH₃ | —H | —CH₃ | |
| 64 | —CH₂CH₃ | p-CHCH₂CH₃<br>    \|<br>    CH₃ | —H | —CH₃ | |
| 65 | —CH₂CH₃ | p-CH₂CH(CH₂)₂CH₃<br>        \|<br>        CH₃ | —H | —CH₂CH₃ | |
| 66 | —CH₂CH₃ | p-(CH₂)₃CH(CH₃)₂ | —H | —CH₂-phenyl | |
| 67 | —CH₂CH₃ | p-(CH₂)₁₀CH₃ | —H | —CH₂-(p-CH₂CH₃-phenyl) | |
| 68 | —CH₂CH₃ | p-O-phenyl | —H | —CH₃ | |

TABLE 1-continued
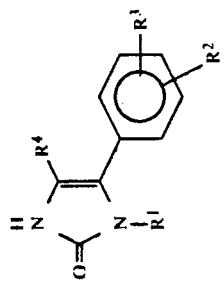
| Compound No. | R¹ | R² | R³ | R⁴ | m.p. (°C.) |
|---|---|---|---|---|---|
| 69 | —CH₂CH₃ | p-O-C₆H₄-Cl | —H | —CH₃ | |
| 70 | —CH₂CH₃ | p-O-C₆H₄-CH₃ | —H | —CH₃ | |
| 71 | —CH₂CH₃ | p-O-C₆H₄-CH(CH₃)₂ | —H | —CH₃ | |
| 72 | —CH₂CH₃ | p-O-C₆H₄-OCH(CH₃)₂ | —H | —CH₃ | |
| 73 | —CH₂CH₃ | m-O-C₆H₄-F | —H | —CH₂CH₃ | |
| 74 | —CH(CH₃)₂ | o-CH₂CH₂CH₃ | —H | —CH₂-C₆H₄-OCH(CH₃)₂ (p) | |

TABLE 1-continued

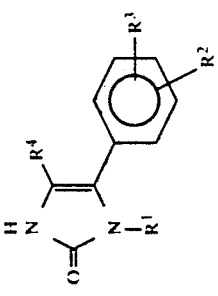

| Compound No. | R¹ | R² | R³ | R⁴ | m.p. (°C.) |
|---|---|---|---|---|---|
| 75 | —CH(CH₃)₂ | m-CH₂CH₂CH₃ | —H | —CH₂-(p-F-phenyl) | |
| 76 | —CH(CH₃)₂ | m-O(CH₂)₃CH₃ | —H | —(CH₂)₂-(p-OCH₂CH₃-phenyl) | |
| 77 | —CH(CH₃)₂ | cyclohexyl | —H | —CH₃ | 274 |
| 78 | —CH(CH₃)₂ | p-(CH₂)₃CH₃ | —H | —CH₃ | 205 |
| 79 | —CH(CH₃)₂ | p-phenyl | —H | —CH₃ | 242 |
| 80 | —CH(CH₃)₂ | o-O(CH₂)₃CH₃ | —H | —CH₃ | 140.5-142 |
| 81 | —CH(CH₃)₂ | p-CH₂CH₂CH₃ | —H | —CH₃ | |
| 82 | —CH(CH₃)₂ | p-(CH₂)₈CH₃ | —H | —CH₃ | |
| 83 | —CH(CH₃)₂ | p-(CH₂)₇CH₃ | —H | —CH₃ | |
| 84 | —CH(CH₃)₂ | p-OCH(CH₃)₂ | —H | —CH₃ | |
| 85 | —CH(CH₃)₂ | m-OCH₂-phenyl | —H | —CH₂CH₃ | |
| 86 | —CH(CH₃)₂ | o-(CH₂)₉CH₃ | —H | —CH₂CH₃ | 134 |
| 87 | —(CH₂)₃ | p-(CH₂)₃CH₃ | —H | —CH₃ | |

TABLE 1-continued

| Compound No. | R¹ | R² | R³ | R⁴ | m.p. (°C.) |
|---|---|---|---|---|---|
| 88 | —(CH₂)₃CH₃ | p-cyclohexyl | —H | —CH₃ | |
| 89 | —(CH₂)₃CH₃ | p-(CH₂)₅CH₃ | —H | —CH₃ | |
| 90 | —(CH₂)₃CH₃ | p-O(CH₂)₁₀CH₃ | —H | —CH₂-phenyl | |
| 91 | cyclopentyl | p-(CH₂)₁₀CH₃ | —H | —CH₃ | |
| 92 | cyclopentyl | p-S(CH₂)₇CH₃ | —H | —(CH₂)₃-phenyl | |
| 93 | cyclohexyl | phenyl | —H | —CH₃ | 248 |
| 94 | cyclohexyl | —O(CH₂)₂CH(CH₃)₂ | —H | —CH₃ | 198-200 |

TABLE 1-continued

| Compound No. | R¹ | R² | R³ | R⁴ | m.p. (°C.) |
|---|---|---|---|---|---|
| 95 | phenyl | p-(CH$_2$)$_3$CH$_3$ | —H | —CH$_2$CH$_3$ | 183-184 |
| 96 | phenyl | p-CH$_2$CH(CH$_3$)$_2$ | —H | —CH$_3$ | 260 |
| 97 | phenyl | p-(CH$_2$)$_4$CH$_3$ | —H | —CH$_3$ | 168 |
| 98 | phenyl | p-(CH$_2$)$_5$CH$_3$ | —H | —CH$_3$ | 142-144 |
| 99 | phenyl | cyclohexyl | —H | —CH$_3$ | 294-297 |
| 100 | phenyl | p-(CH$_2$)$_6$CH$_3$ | —H | —CH$_3$ | 154 |

TABLE 1-continued
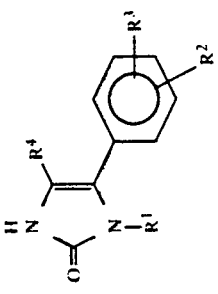
| Compound No. | $R^1$ | $R^2$ | $R^3$ | $R^4$ | m.p. (°C.) |
|---|---|---|---|---|---|
| 101 | ⟨H⟩ | p-(CH$_2$)$_7$CH$_3$ | —H | —CH$_3$ | 166–167 |
| 102 | ⟨H⟩ | p-(CH$_2$)$_9$CH$_3$ | —H | —CH$_3$ | 146 |
| 103 | ⟨H⟩ | p-(CH$_2$)$_{11}$CH$_3$ | —H | —CH$_3$ | 142 |
| 104 | ⟨H⟩ | p-(CH$_2$)$_{13}$CH$_3$ | —H | —CH$_3$ | 140 |
| 105 | ⟨H⟩ | p-(CH$_2$)$_{17}$CH$_3$ | —H | —CH$_3$ | 130 |
| 106 | ⟨H⟩ | p-CH$_2$CH$_2$CH$_3$ | —H | —CH$_3$ | 226–228 |

TABLE 1-continued
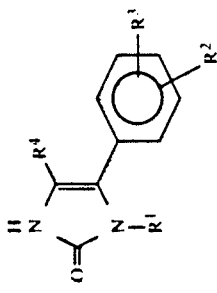
| Compound No. | R¹ | R² | R³ | R⁴ | m.p. (°C.) |
|---|---|---|---|---|---|
| 107 | (cyclohexyl) | m-OCH(CH₃)₂ | —H | —CH₃ | 191-192 |
| 108 | (cyclohexyl) | o-OCH(CH₃)₂ | —H | —CH₃ | 156-158.5 |
| 109 | (cyclohexyl) | p-OCH(CH₃)₂ | —H | —CH₃ | 259-260 |
| 110 | (cyclohexyl) | m-O(CH₂)₃CH₃ | —H | —CH₃ | 175.5-176.5 |
| 111 | (cyclohexyl) | p-O(CH₂)₃CH₃ | —H | —CH₃ | 173-175 |
| 112 | (cyclohexyl) | p-O(CH₂)₄CH₃ | —H | —CH₃ | 206-207 |

TABLE 1-continued
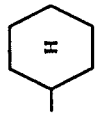
| Compound No. | R¹ | R² | R³ | R⁴ | m.p. (°C.) |
|---|---|---|---|---|---|
| 113 | phenyl | p-(CH$_2$)$_3$CH$_3$ | —H | —CH$_3$ | 152–154 |
| 114 | phenyl | p-O(CH$_2$)$_5$CH$_3$ | —H | —CH$_3$ | 173–174 |
| 115 | phenyl | p-O(CH$_2$)$_6$CH$_3$ | —H | —CH$_3$ | 175–176 |
| 116 | phenyl | p-O(CH$_2$)$_7$CH$_3$ | —H | —CH$_3$ | 143–144 |
| 117 | phenyl | p-O(CH$_2$)$_8$CH$_3$ | —H | —CH$_3$ | 152 |
| 118 | phenyl | p-O(CH$_2$)$_{11}$CH$_3$ | —H | —CH$_3$ | 125–126 |

TABLE 1-continued

| Compound No. | R¹ | R² | R³ | R⁴ | m.p. (°C) |
|---|---|---|---|---|---|
| 119 | phenyl | p-O(CH₂)₁₇CH₃ | —H | —CH₃ | 123-124 |
| 120 | phenyl | p-O(CH₂)₃-phenyl | —H | —CH₃ | 216-218 |
| 121 | phenyl | p-S(CH₂)₃CH₃ | —H | —CH₃ | 147-150 |
| 122 | phenyl | p-O(CH₂)₉CH₃ | —H | —CH₃ | 137-138 |
| 123 | phenyl | p-O-phenyl | —H | —CH₃ | 198 |
| 124 | phenyl | p-OCH₂-phenyl | —H | —CH₃ | 262 |

TABLE 1-continued

| Compound No. | R¹ | R² | R³ | R⁴ | m.p. (°C.) |
|---|---|---|---|---|---|
| 125 | phenyl | p-CH₂CH₂CH₃ | —H | —CH₃ | 240–242 |
| 126 | phenyl | p-(CH₂)₃CH₃ | —H | —CH₃ | 215–217 |
| 127 | phenyl | p-(CH₂)₅CH₃ | —H | —CH₃ | 200.5–202.5 |
| 128 | phenyl | p-OCH(CH₃)₂ | —H | —CH₃ | 288–290 |
| 129 | phenyl | p-O(CH₂)₃CH₃ | —H | —CH₃ | 199–202 |
| 130 | phenyl | p-O(CH₂)₇CH₃ | —H | —CH₃ | 186–187 |

TABLE 1-continued
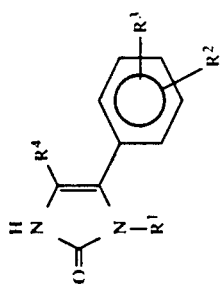
| Compound No. | R¹ | R² | R³ | R⁴ | m.p. (°C.) |
|---|---|---|---|---|---|
| 131 | phenyl | cyclohexyl-H | —H | —$CH_3$ | |
| 132 | phenyl | p-$CH_2CH_3$-phenyl | —H | —$CH_3$ | |
| 133 | phenyl | p-Br-phenyl | —H | —$CH_3$ | |
| 134 | phenyl | p-$(CH_2)_{15}CH_3$ | —H | —$CH_3$ | |
| 135 | phenyl | p-$O(CH_2)_{14}CH_3$ | —H | —$CH(CH_3)_2$ | |
| 136 | phenyl | p-$O(CH_2)_3$-phenyl | —H | —$(CH_2)_3CH_3$ | |

TABLE 1-continued
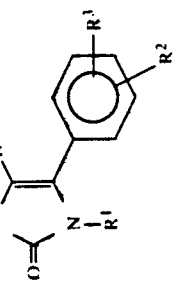
| Compound No. | R¹ | R² | R³ | R⁴ | m.p. (°C.) |
|---|---|---|---|---|---|
| 137 | —CH₂—(phenyl) | p-(CH₂)₃CH₃ | —H | —CH₃ | 155.5–156 |
| 138 | —CH₂—(phenyl) | p-C(CH₃)₃ | —H | —CH₃ | 229–230 |
| 139 | —CH₂—(phenyl) | p-(CH₂)₅CH₃ | —H | —CH₃ | 123 |
| 140 | —CH₂—(phenyl) | p-(cyclohexyl) | —H | —CH₃ | 272 |
| 141 | —CH₂—(phenyl) | p-(phenyl) | —H | —CH₃ | 228 |
| 142 | —CH₂—(phenyl) | p-O(CH₂)₃CH₃ | —H | —CH₃ | 157–158 |

TABLE 1-continued

| Compound No. | R¹ | R² | R³ | R⁴ | m.p. (°C.) |
|---|---|---|---|---|---|
| 143 | —CH₂—C₆H₅ | p-(CH₂)₄CH₃ | —H | —CH₃ | |
| 144 | —CH₂—C₆H₅ | p-(CH₂)₁₂CH₃ | —H | —CH₃ | |
| 145 | —CH₂—C₆H₅ | p-O(CH₂)₅CH₃ | —H | —CH₃ | |
| 146 | —CH₂—C₆H₅ | p-O(CH₂)₁₃CH₃ | —H | —CH₃ | |
| 147 | —CH₂—C₆H₅ | p-O—C₆H₅ | —H | —CH₃ | |
| 148 | —CH₂—C₆H₅ | p-OCH₂—C₆H₅ | —H | —CH₃ | |

TABLE 1-continued

[Structure shown: imidazolinone with R¹, R², R³, R⁴ substituents]

| Compound No. | R¹ | R² | R³ | R⁴ | m.p. (°C.) |
|---|---|---|---|---|---|
| 149 | —CH₂—(phenyl) | p-O(CH₂)₂(phenyl) | —H | —CH₃ | |
| 150 | cycloheptyl-H | p-(CH₂)₁₄CH₃ | —H | —CH₃ | |
| 151 | cycloheptyl-H | p-OCH₂(phenyl) | —H | —CH(CH₃)₂ | |
| 152 | —(CH₂)₅CH₃ | p-(CH₂)₁₆CH₃ | —H | —CH₃ | |
| 153 | —(CH₂)₅CH₃ | cyclohexyl-H | —H | —CH₃ | |
| 154 | —(CH₂)₅CH₃ | p-O(CH₂)₁₂CH₃ | —H | —CH₃ | |
| 155 | —(CH₂)₇CH₃ | p-O(phenyl) | —H | —CH₂(phenyl) | |

TABLE 1-continued

| Compound No. | R¹ | R² | R³ | R⁴ | m.p. (°C.) |
|---|---|---|---|---|---|
| 156 | —(CH₂)₂-phenyl | p-(CH₂)₁₈CH₃ | —H | —CH₃ | |
| 157 | —(CH₂)₂-phenyl | p-(CH₂)₅CH₃ | —H | —CH₂CH₃ | |
| 158 | —(CH₂)₂-phenyl | p-O(CH₂)₇CH₃ | —H | —CH₃ | |
| 159 | —(CH₂)₂-phenyl | p-OCH₂-phenyl | —H | —CH₃ | |
| 160 | —(CH₂)₂-phenyl | p-SCH(CH₃)₂ | —H | —CH₃ | |
| 161 | —CH₃ | o-(CH₂)₇CH₃ | —H | —CH₃ | |
| 162 | —CH₃ | m-(CH₂)₆CH₃ | —H | —CH₃ | |
| 163 | —CH₃ | m-cyclohexyl | —H | —CH₃ | |

TABLE 1-continued
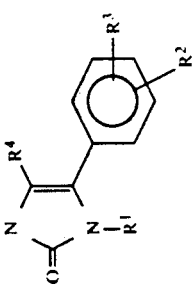
| Compound No. | R¹ | R² | R³ | R⁴ | m.p. (°C.) |
|---|---|---|---|---|---|
| 164 | —CH₃ | (phenyl) | —H | —CH₃ | |
| 165 | —CH₃ | o-O(CH₂)₉CH₃ | —H | —CH₃ | |
| 166 | —CH₃ | m-O(CH₂)₁₅CH₃ | —H | —CH₃ | |
| 167 | —CH₃ | p-CH=CHCH₃ | —H | —CH₃ | |
| 168 | —CH₃ | p-CH₂CH=CHCH₃ | —H | —CH₃ | |
| 169 | —CH₃ | p-CH=CH(CH₂)₃CH₃ | —H | —CH₃ | |
| 170 | —(CH₂)₆CH₃ | p-CH=CH(CH₂)₇CH₃ | —H | —CH₃ | |
| 171 | —CH₂CH₃ | p-CH=CH(CH₂)₉CH₃ | —H | —CH₂CH₃ | |
| 172 | (cyclohexyl) | p-CH=CH(CH₂)₁₄CH₃ | —H | (cyclohexyl) | |
| 173 | —CH₂(phenyl) | p-CH=CH(CH₂)₁₇CH₃ | —H | —CH₃ | |
| 174 | —CH₂(phenyl) | p-C≡CCH₂CH₃ | —H | —CH₃ | |

TABLE 1-continued

[Structure: phenyl ring with R³ and R² substituents, connected via C=C to N-H and N-R¹ with C=O, and R⁴ group]

| Compound No. | R¹ | R² | R³ | R⁴ | m.p. (°C.) |
|---|---|---|---|---|---|
| 175 | —CH₂—(phenyl) | p-C≡C(CH₂)₇CH₃ | —H | —CH₃ | |
| 176 | —CH₃ | p-C≡C(CH₂)₇CH₃ | —H | —CH₃ | |
| 177 | —CH₃ | p-C≡C(CH₂)₈CH₃ | —H | —CH₃ | |
| 178 | —CH₃ | p-C≡C(CH₂)₁₂CH₃ | —H | —CH₃ | |
| 179 | —CH(CH₃)₂ | p-C≡C(CH₂)₁₅CH₃ | —H | —CH₃ | |
| 180 | —CH(CH₃)₂ | p-C≡C(CH₂)₁₇CH₃ | —H | —CH₃ | |
| 181 | —CH(CH₃)₂ | p-OCH₂CH=CH₂ | —H | —CH₃ | |
| 182 | —CH(CH₃)₂ | p-OCH₂CH=C(CH₃)₂ | —H | —CH₃ | |
| 183 | cyclohexyl | p-O-CH₂-CH=C(CH₃)-(CH₂)₂-CH=C(CH₃)-CH₃ (geranyl) | —H | —CH₃ | |
| 184 | cyclohexyl | p-OCH₂CH=CH(CH₂)₁₃CH₃ | —H | —CH₃ | |
| 185 | cyclohexyl | p-OCH₂CH=CH(CH₂)₁₆CH₃ | —H | —CH₃ | |
| 186 | —CH₂CH₃ | p-OCH₂C≡CCH₃ | —H | —CH₃ | |
| 187 | —CH₂CH₃ | p-OCH₂C≡C(CH₂)₃CH₃ | —H | —CH₃ | |
| 188 | —CH₂CH₃ | p-OCH₂C≡C(CH₂)₈CH₃ | —H | —CH₃ | |

TABLE 1-continued

[Structure: imidazolin-2-one with R¹ on N, R² and R³ on phenyl attached at 4-position, R⁴ at 5-position]

| Compound No. | R¹ | R² | R³ | R⁴ | m.p. (°C.) |
|---|---|---|---|---|---|
| 189 | phenyl | p-OCH₂C≡C(CH₂)₁₂CH₃ | —H | —CH(CH₃)₂ | |
| 190 | phenyl | p-OCH₂C≡C(CH₂)₁₆CH₃ | —H | —CH(CH₃)₂ | |
| 191 | —CH₂CH=CH₂ | p-(CH₂)₃CH₃ | —H | —CH₃ | |
| 192 | —CH₂CH=CH(CH₂)₂CH₃ | p-(CH₂)₃CH₃ | —H | —CH₃ | |
| 193 | —(CH₂)₆CH=CH₂ | p-(CH₂)₃CH₃ | —H | —CH₃ | |
| 194 | —CH₂C≡CH | p-OCH₂CH=CH(CH₂)₁₀CH₃ | —H | —CH₃ | |
| 195 | —CH₂C≡CCH₃ | p-phenyl-OCH₂CH₃ | —H | —CH₃ | |
| 196 | p-CH₃-phenyl | p-OCH₂C≡C(CH₂)₁₀CH₃ | —H | —CH₃ | |
| 197 | p-OCH₃-phenyl | p-CH₂-phenyl | —H | —CH₃ | |

TABLE 1-continued

[Structure: imidazolinone with R¹, R², R³, R⁴ substituents]

| Compound No. | R¹ | R² | R³ | R⁴ | m.p. (°C.) |
|---|---|---|---|---|---|
| 198 | 3-F-C₆H₄-CH₂- | p-CH₃-C₆H₄- | —H | —CH₃ | |
| 199 | 2-Cl-C₆H₄- | p-F-C₆H₄-(CH₂)₂- | —H | —CH₃ | |
| 200 | p-CH₃-C₆H₄-CH₂- | p-Cl-C₆H₄-(CH₂)₃- | —H | —CH₃ | |
| 201 | p-CH₂CH₂CH₃-C₆H₄-CH₂- | p-OCH₃-C₆H₄-(CH₂)₂- | —H | —CH₃ | |
| 202 | p-OCH₃-C₆H₄-(CH₂)₂- | p-O(CH₂)₁₂CH₃-C₆H₄- | —H | —CH₃ | |
| 203 | p-Br-C₆H₄-CH₂- | p-O(CH₂)₁₆CH₃-C₆H₄- | —H | —CH₃ | |
| 204 | p-iPr-C₆H₄- | p-O(CH₂)₁₉CH₃-C₆H₄- | —H | —CH₃ | |

TABLE 2

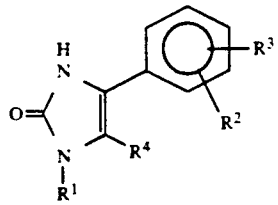

| Compound No. | R¹ | R² | R³ | R⁴ | m.p. (°C.) |
|---|---|---|---|---|---|
| 205 | cyclohexyl-H | p-(CH$_2$)$_3$CH$_3$ | —H | —CH$_3$ | 236 |
| 206 | —CH$_3$ | p-(CH$_2$)$_5$CH$_3$ | —H | —CH$_3$ | |
| 207 | —CH$_3$ | p-cyclohexyl-H | —H | —CH$_2$CH$_3$ | |
| 208 | —CH$_2$CH$_2$CH$_3$ | p-phenyl | —H | —CH(CH$_3$)$_2$ | |
| 209 | —(CH$_2$)$_3$CH$_3$ | p-(CH$_2$)$_9$CH$_3$ | —H | —C(CH$_3$)$_3$ | |
| 210 | —(CH$_2$)$_5$CH$_3$ | o-CH$_2$CH$_2$CH$_3$ | —H | —CH$_2$-phenyl | |
| 211 | cyclohexyl-H | m-(CH$_2$)$_{14}$CH$_3$ | —H | —(CH$_2$)$_5$CH$_3$ | |
| 212 | —phenyl | p-O(CH$_2$)$_3$CH$_3$ | —H | cyclohexyl-H | |
| 213 | —CH$_2$-phenyl | p-OCH$_2$-phenyl | —H | —(CH$_2$)$_2$-phenyl | |
| 214 | —CH$_2$-phenyl | p-O-phenyl | —H | —CH$_3$ | |
| 215 | —CH$_2$-phenyl | p-O(CH$_2$)$_9$CH$_3$ | —H | —CH$_3$ | |
| 216 | —CH$_3$ | p-O(CH$_2$)$_{19}$CH$_3$ | —H | —CH$_3$ | |

TABLE 3

[Structure: imidazoline with MO-, N, R¹, R⁴, and phenyl-R²/R³ substituents]

| Compound No. | R¹ | R² | R³ | R⁴ | M | m.p. (°C.) |
|---|---|---|---|---|---|---|
| 217 | —CH₃ | p-cyclohexyl | —H | —CH₃ | Na | >300 |
| 218 | —CH₃ | p-(CH₂)₃CH₃ | —H | —CH₃ | Na | |
| 219 | —CH₃ | p-(CH₂)₅CH₃ | —H | —CH₃ | Na | |
| 220 | —CH₃ | p-phenyl | —H | —CH₃ | Na | |
| 221 | cyclohexyl | p-(CH₂)₃CH₃ | —H | —CH₃ | Na | |
| 222 | cyclohexyl | p-O(CH₂)₃CH₃ | —H | —CH₃ | Na | |
| 223 | —CH₂-phenyl | p-(CH₂)₃CH₃ | —H | —CH₃ | Na | |

The 4-imidazolin-2-one derivatives (I) of the present invention may be produced by procedures known to those skilled in the art. However, the compounds (I) which bear R⁴ at 4-position and a substituted phenyl at 5-position, said special compounds being referred to herein as compounds (Ia), may be produced in the manner as shown in the following synthetic scheme I.

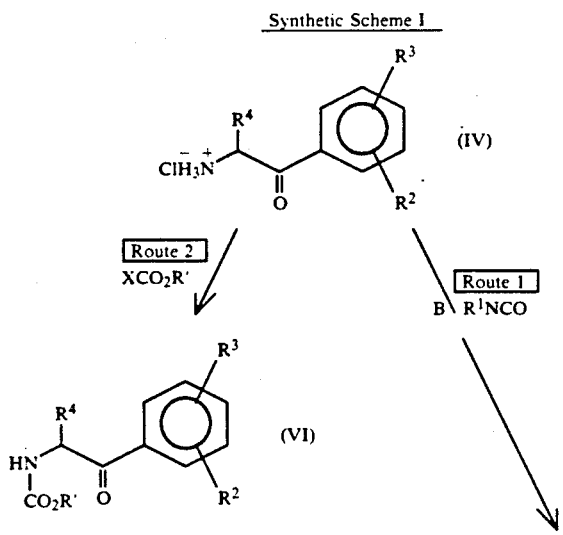

Synthetic Scheme I

-continued

Synthetic Scheme I

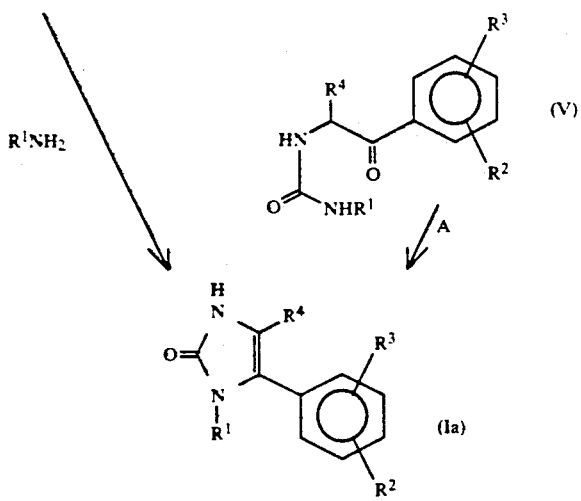

wherein $R^1$, $R^2$, $R^3$ and $R^4$ are as hereinbefore defined, A and B represent an acid and a base respectively.

According to Route 1 in Scheme I, α-aminoketone hydrochloride (IV) is allowed to react with isocyanate in the presence of a base and a nonreactive solvent to obtain ketourea (V). Suitable nonreactive solvents include hydrocarbons such as benzene, toluene, and xylene; ethers such as ethyl ether, isopropyl ether, tetrahydrofuran (THF), and dioxane; ketons such as acetone and methyl ethyl ketone; and esters such as methyl acetate and ethyl acetate. Reaction temperature ranges from $-20°$ C. to a boiling point of the solvent used, a temperature between $0°$ C. and $80°$ C. being preferred. Suitable bases are inorganic bases such as potassium carbonate and sodium bicarbonate; and organic bases such as triethylamine and pyridine.

Ring closure of the resulting ketourea (V) gives a 4-imidazolin-2-one derivative (Ia) of the invention. The ring closure reaction does not necessarily require the addition of an acid. However, when used, the acid can be an inorganic acid such as sulfuric acid or phosphoric acid; an organic acid such as trifluoroacetic acid, methanesulfonic acid, or p-toluenesulfonic acid; or an inorganic Lewis acid such as aluminium chloride or tin tetrachloride. The use of a reaction solvent is not essential either. However, when used, a solvent nonreactive to both the ketourea (V) and the just-mentioned acids, such as the foregoing hydrocarbons, ethers, ketons, halogenated hydrocarbons such as chloroform, dichloromethane, an dichloroethane, is preferred. Preferred reaction temperature ranges from $0°$ C. to $250°$ C.

In accordance with Route 2 in Scheme I, α-aminoketone hydrochloride (IV) is treated with an acylating agent such as diethyl carbonate, ethyl chloroformate, or methyl chloroformate to obtain ketocarbamate (VI). This reaction is preferably conducted in the presence of a solvent selected from the foregoing hydrocarbons, ethers, and halogenated hydrocarbons at temperature between $0°$ C. and $100°$ C. The thus obtained ketocarbamate (VI) is reacted with a primary amine to give a 4-imidazolin-2-one derivative (Ia). The reaction may be carried out in the presence of a solvent selected from the foregoing hydrocarbons, ethers, dimethylformamide, and dimethylacetamide, although the use of the solvent is not essential. This reaction is preferably conducted in the presence of an acid or a base as a catalyst. Preferred temperature is $0°$ C. to $250°$ C.

The compounds (I) which bear a substituted phenyl at 4-position and $R^4$ at 5-position, such compounds being referred to as compound (Ib), may be produced in the manner as shown in the following synthetic scheme II.

Synthetic Scheme II

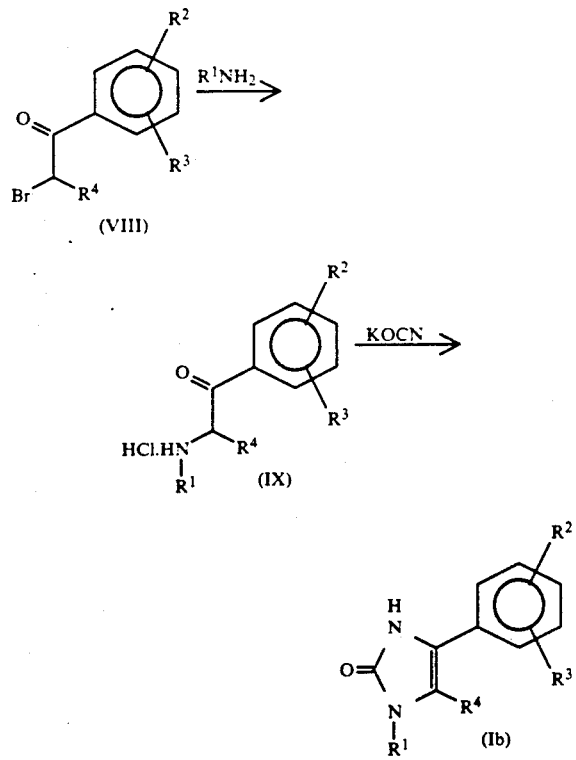

wherein $R^1$, $R^2$, $R^3$ and $R^4$ are as defined in the foregoing.

The compound (Ib) of the invention may be synthesized by the reaction of α-aminoketone hydrochloride (IX), which can be produced by the reaction of α-bromoketone (VIII) and a primary amine, with a cyanic acid salt such as potassium cyanate. The reaction may be carried out in the presence of a solvent, preferably an alcohol such as methanol or ethanol, at temperature between 0° C. and a boiling temperature of the solvent employed, with a temperature of 0° C.-80° C. being preferred.

The compounds of the invention thus produced may be readily isolated by recognized methodologies, such as silica gel chromatography and recrystalization.

The compound (I) of the invention in the form of 4-imidazolin-2-one derivative is easily converted to its enol form (II). The present invention covers both keto and enol forms as previously mentioned. The compounds of the invention are useful as a lipoperoxidation-inhibitor, radical scavenger, and memory-improving agent.

As will be illustrated in the Examples hereinafter, in vitro test employing rat brain homogenate revealed that the compounds of the invention had stronger lipoperoxidation-inhibitory and radical-scavenging activities than idebenone and dihydroergotoxine which have been clinically employed for cerebrovascular diseases such as memory insufficiency or cognitive disorder. Passive avoidance response test in mice also showed memory-improving activity of the compounds of the invention. On the other hand, the compounds of the invention are less toxic.

Accordingly, the compounds of the invention may be useful for prophylactic or therapeutic treatment of a variety of ischemic and ischemic-related diseases, for example, brain diseases such as cerebrovascular diseases (e.g., cerebral infarction and cerebral apoplexy), cerebral dysfunction and vascular dementia deduced therefrom, and pathological change of cerebral vascular and tissue caused by aging, ischemic heart diseases such as cardiac infarction and heart failure attributable to ischemia of cardiac muscle, peripheral circulatory disorders or inflammatory such as ischemic nephropathy, ischemic digestive disorder, atherosclerosis, oxygen-poisoned lung (acute lung injury), and neurodegeneration diseases such as dementia based on polyinfarctus cerebral atherosclerosis and Alzheimer's dementia.

The compounds of this invention are preferably formulated prior to administration using pharmaceutically acceptable carriers, diluents or excipients therefor. The amount of the compound of the invention in the pharmaceutical formulation can vary from 1% to 90% by weight. The compositions can be in the form of granules, microgranules, powders, tablets, soft and hard gelatin capsules, syrups, emulsions, suspensions, solutions, and the like, for oral administration, and sterile injectable solutions for intravenous, intramuscular or subcutaneous administration, and suppositories for rectal administration. The compositions can also be sterile packaged powders which are diluted with sterile distilled water when used for injection.

Pharmaceutically acceptable carriers, diluents or excipients used for the production of the formulation can be organic or inorganic solids, semisolids, or liquids suitable for oral or parenteral administration. Examples of suitable carriers, excipients, and diluents employable for the production of solid formulations are lactose, sucrose, starches, talc, cellulose, dextrin, kaolin, calcium carbonate, and the like. Liquid formulations for oral administration, such as emulsions, syrups, suspensions, and solutions, are prepared by the use of conventional inert diluents such as water or vegetable oil. The formulations may additionally include wetting agents, suspending agents, sweetening agents, flavoring agents, coloring agents, preserving agents, and the like.

Solvents or suspending agents used for the production of the formulations for parenteral administration, such as injectable solutions and suppositories, include water, propylene glycol, polyethylene glycol, benzyl alcohol, ethyl oleate, lecithin, and the like. Also, the compounds can be used as a cyclodextrin clathrate compound thereof or through procedure of incorporating it in a liposome. Suitable bases for suppositories include, for example, cacao butter, emulsified cacao butter, laurin tallow, witepsol, and the like.

The pharmaceutical formulations mentioned above are prepared by procedures well known to those skilled in the art.

The specific clinical dose for adults of the compound of the invention will generally range from 0.01 mg to 1000 mg per day for oral administration, with 0.01–100 mg/day being preferred. However, the specific dose will, of course, be determined by the particular circumstances surrounding the case, including, for example, age of the individual patient, the condition being treated, the route of administration, and the like. The daily dose can be administered in a single dose or in multiple doses throughout the day, for example, bid. or tid. The formulation can also be administered every other day.

Daily dose for injection will range between 0.001 mg and 100 mg, and can be administered continuously or at regular intervals.

The following Preparations and Examples further illustrate the compounds of the present invention and methods for their production. The Examples are not intended to be limiting to the scope of the invention in any respect and should not be so construed. The terms "m.p.", "IR", "NMR", and "MS" mean melting point, infrared spectrum, nuclear magnetic resonance spectrum, and mass spectrum, respectively.

PREPARATION 1

4'-Isoamyloxy-2-trifluoroacetylaminopropiophenone

4'-Isoamyloxypropiophenone (100 g, 45.5 mmol) was dissolved in chloroform (100 ml), and bromine (7.63 g, 47.7 mmol) was dropwise added thereto under ice-cooling. The mixture was stirred for 3 hours, and poured into water after disappearance of bromine colour. The aqueous mixture was extracted with dichloromethane, and the extract was washed with saturated aqueous sodium chloride and dried over magnesium sulfate. The solvent was evaporated off, which gave a crude intermediate product. The product was dissolved, without purification, in acetone (100 ml) followed by the addition of trifluoroacetamide (10.2 g, 90 mmol) and anhydrous potassium carbonate (12.4 g, 90 mmol). After 1.5 hours heating under reflux, the mixture was cooled to room temperature, and the acetone was evaporated off. The residue was taken in dichloromethane, and the organic solution was washed with saturated aqueous sodium chloride and dried over anhydrous magnesium sulfate. Evaporation of the organic solvent provided a crude product which was purified by silica gel chromatography. The title compound was thus obtained. Yield: 4.44 g (29%).

NMR (CDCl$_3$)$\delta$(ppm): 7.96 (d, 2 H, 9 Hz), 6.98 (d, 2 H, 9 Hz), 5.48 (t, 1 H, 7 Hz), 4.08 (t, 2 H, 6.7 Hz), 1.65–1.95 (m, 3 H), 1.52 (d, 3 H, 7 Hz), 0.98 (d, 6 H, 6.5 Hz).

PREPARATION 2

2-Amino-4'-isoamyloxypropiophenone

4'-Isoamyloxy-2-trifluoroacetylaminopropiophenone (4.0 g, 12.1 mmol) obtained in Preparation 1 was dissolved in ethanol (50 ml). The solution, after addition of conc. HCl (10 ml), was heated under reflux for 4 hours. Evaporation of the ethanol gave crystals which were then washed with chloroform to give the title compound. Yield; 2.25 g (69%).

NMR (DMSOd$_6$)δ(ppm): 8.57 (s, 3 H), 8.04 (d, 2 H, 9 Hz), 7.11 (d, 2 H, 9 Hz), 5.05 (q, 1 H, 7 Hz), 4.13 (t, 2 H, 7 Hz), 1.80 (hep, 1 H, 7 Hz), 1.65 (q, 2 H, 7 Hz), 1.44 (d, 3 H, 7 Hz), 0.94 (d, 6 H, 7 Hz).

EXAMPLE 1

1-Cyclohexyl-5-(4'-isoamyloxyphenyl)-4-methyl-4-imidazolin-2-one (Coumpound No. 94)

2-Amino-4'-isoamyloxypropiophenone hydrochloride (543 mg, 2.0 mmol) obtained in Preparation 2 was suspended in acetone (20 ml) under ice-cooling, and cyclohexyl isocyanate (275 mg, 2.2 mmol) was added thereto. To the mixture was added triethylamine (1.11 ml, 8.0 mmol), and the mixture was stirred for 3 hours, while gradually warming to room temperature. Trifluoroacetic acid (2 ml) was then added, stirring was continued an additional one hour, and the solvent was distilled off under vacuum. The residue was taken in chloroform and the chloroform phase was washed with saturated aqueous sodium bicarbonate and dried over magnesium sulfate. Evaporation of the solvent gave a crude product, which was then purified by silica gel chromatography to obtain the title compound. Yield: 520 mg (76%), m.p. 198°-200° C.

IR (KBr) (cm$^{-1}$) 1675, 1520, 1375, 1250, 1180.

NMR (CDCl$_3$)δ(ppm): 9.11 (s, 1 H), 7.14 (d, 2 H, 8.7 Hz), 6.93 (d, 2 H, 8.7 Hz), 4.03 (t, 2 H, 6.7 Hz), 3.4-3.6 (m, 1 H), 2.0-2.3 (m, 2 H), 1.93(s, 3 H), 1.87 (hep, 1 H, 6.5 Hz), 1.4-1.8 (m, 8 H), 1.0-1.3 (m, 2 H), 0.99 (d, 6 H, 6.5 Hz).

In a manner as analogous to that described in Example 1, Coumpound Nos. 3-33, 54-61, 78-80, 87, 95-121, 125-130, and 138-142 listed in the foregoing Table 1 were prepared.

EXAMPLE 2

5-(4'-n-Butylphenyl)-1,4-dimethyl-4-imidazolin-2-one (Compound No. 2)

2-Amino-4'-n-butylpropiophenone hydrochloride (5.36 g, 22.2 mmol) was suspended in acetone (180 ml) under ice-cooling, and methyl isocyanate (1.61 g, 28.2 mmol) was added thereto. After addition of triethylamine (4.49 g, 44.5 mmol), the mixture was stirred for 40 minutes under ice-cooling. Trifluoroacetic acid (16 ml) was added thereto, and the mixture was stirred for 5 hours at room temperature. The solvent was removed by evaporation under vacuum, and the residue was taken in dichloromethane. The organic mixture was washed successively with water and saturated aqueous sodium chloride, and dried over magnesium sulfate. Evaporation of the solvent provided a crude product, which was purified by column chromatography (chloroform/ ethanol = 50/1 (v/v)) and recrystalization (hexane-ethyl acetate) to give the title compound. Yield: 3.85 g (71%), m.p. 180°-180.5° C.

IR (KBr) (cm$^{-1}$): 1680, 1520, 1440, 1390, 750.

NMR (CDCl$_3$)δ(ppm): 7.28 (d, 2 H, 8 Hz), 7.16 (d, 2 H, 8 Hz), 3.22 (s, 3 H), 2.66 (t, 2 H, 8 Hz), 2.10 (s, 3 H), 1.6-1.8 (m, 2 H), 1.3-1.5 (m, 2 H), 0.95 (t, 3 H, 7 Hz).
MS (m/e): 244 (M$^+$), 201, 144, 116.

EXAMPLE 3

1-Benzyl-5-(4'-n-butylphenyl)-4-methyl-4-imidazolin-2-one (Compound No. 137)

2-Amino-4'-n-butylpropiophenone hydrochloride (4.41 g, 18.3 mmol) was suspended in acetone (180 ml) under ice-cooling, and benzyl isocyanate (3.03 g, 22.8 mmol) was added thereto. Triethylamine (3.83 g, 37.9 mmol) was added, and the mixture was stirred for 50 minutes under ice-cooling. After addition of trifluoroacetic acid (12 ml), the mixture was stirred overnight at room temperature. The solvent was removed by evaporation in vacuo, and the residue was extracted with dichloromethane. The extract was washed successively with water and saturated aqueous sodium chloride, and dried over anhydrous magnesium sulfate. Evaporation of the solvent provided a crude product, which was purified by column chromatography (chloroform/ethanol = 50/1 (v/v)) and recrystalization (ethyl acetate) to give the title compound. Yield: 4.76 g (81%), m.p. 155.5°-156° C.

IR (KBr) (cm$^{-1}$) 1675, 1520, 1415, 1400, 1360.

NMR (CDCl$_3$)δ(ppm): 7.0-7.3 (m, 9 H), 4.79 (s, 2 H), 2.61 (t, 2 H, 8 Hz), 2.04 (s, 3 H), 1.5-1.8 (m, 2 H), 1.2-1.5 (m, 2 H), 0.94 (t, 3 H, 7 Hz).

EXAMPLE 4

5-(4'-Cyclohexylphenyl)-1-isopropyl-4-methyl-4-imidazolin-2-one (Compound No. 77)

2-Amino-4'-cyclohexylpropiophenone hydrochloride (477 mg, 1.78 mmol) was suspended in acetone (30 ml) under ice-cooling, and isopropyl isocyanate (198 mg, 2.33 mmol) was added thereto. Triethylamine (533 mg, 5.28 mmol) was added, and the mixture was stirred for one hour under ice-cooling. After addition of trifluoroacetic acid (2 ml), the mixture was stirred for 2 days at room temperature. The solvent was removed by evaporation in vacuo, and the residue was extracted with dichloromethane. The extract was washed successively with water and saturated aqueous sodium chloride, and dried over magnesium sulfate. Evaporation of the solvent provided a crude product, which was purified by column chromatography (chloroform/ ethanol = 50/1 (v/v)) and recrystalization (ethanol-chloroform) to give the title compound. Yield: 351 mg (66%), m.p. 274° C.

IR (KBr) (cm$^{-1}$): 1680, 1520, 1450, 1410, 1380, 1360, 1330, 1200, 1155.

NMR (CDCl$_3$)δ(ppm): 9.39 (s, 1 H), 7.29 (d, 2 H, 9 Hz), 7.15 (d, 2 H, 9 Hz), 3.9-4.1 (m, 1 H), 2.4-2.6 (m, 2 H), 1.96 (s, 3 H), 1.7-2.2 (m, 6 H), 1.41 (d, 6 H, 7 Hz), 1.2-1.6 (m, 2 H).

EXAMPLE 5

1-Cyclohexyl-5-(4-biphenyl)-4-methyl-4-imidazolin-2-one (Compound No. 93)

2-Amino-4'-phenylpropiophenone hydrochloride (577 mg, 2.21 mmol) was suspended in acetone (30 ml) under ice-cooling, and cyclohexyl isocyanate (334 mg, 2.67 mmol) was added thereto. Triethylamine (608 mg, 6.02 mmol) was then added, and the mixture was stirred for 45 minutes under ice-cooling. After addition of trifluoroacetic acid (2 ml), the mixture was stirred overnight at room temperature. The solvent was removed by evaporation in vacuo, and the residue was extracted with dichloromethane. The extract was washed successively with water and saturated aqueous sodium chloride, and dried over anhydrous magnesium sulfate. Evaporation of the solvent provided a crude product, which was purified by recrystalization (ethanol-chloroform) to give the title compound. Yield: 629 mg (86%), m.p. 248° C.

IR (KBr) (cm$^{-1}$): 1670, 1485, 1450, 1405, 1365.

NMR (CDCl$_3$)δ(ppm): 9.41 (s, 1 H), 7.2–7.7 (m, 9 H), 3.4–3.7 (m, 1 H), 2.1–2.5 (m, 2 H), 2.02 (s, 3 H), 1.4–2.0 (m, 6 H), 1.0–1.4 (m, 2 H).

EXAMPLE 6

1-Cyclohexyl-4-methyl-5-(4'-phenoxyphenyl)-4-imidazolin-2-one (Compound No. 123)

2-Amino-4'-phenoxypropiophenone hydrochloride (459 mg, 1.65 mmol) was suspended in acetone (30 ml) under ice-cooling, and cyclohexyl isocyanate (278 mg, 2.22 mmol) was added thereto. Triethylamine (476 mg, 4.71 mmol) was added, and the mixture was stirred for 50 minutes under ice-cooling. After addition of trifluoroacetic acid (1.5 ml), the mixture was stirred for 3 days at room temperature. The solvent was removed by evaporation in vacuo, and the residue was extracted with dichloromethane. The extract was washed successively with water and saturated aqueous sodium chloride, and dried over anhydrous magnesium sulfate. Evaporation of the solvent provided a crude product, which was purified by column chromatography (chloroform/ethanol = 50/1 (v/v)) and recrystalization (ethyl acetate) to give the title compound. Yield: 520 mg (90%), m.p. 198° C.

IR (KBr) (cm$^{-1}$): 1670, 1585, 1510, 1490, 1365, 1240, 1160.

NMR (CDCl$_3$)δ(ppm): 9.73 (s, 1 H), 7.0–7.4 (m, 9 H), 3.17 (s, 3 H), 2.08 (s, 3 H).

EXAMPLE 7

5-(4'-Benzyloxyphenyl)-1-cyclohexyl-4-methyl-4-imidazolin-2-one (Compound No. 124)

2-Amino-4'-benzyloxypropiophenone hydrochloride (349 mg, 1.20 mmol) was suspended in acetone (30 ml) under ice-cooling, and cyclohexyl isocyanate (204 mg, 1.62 mmol) was added thereto. Triethylamine (377 mg, 3.73 mmol) was then added, and the mixture was stirred for one hour under ice-cooling. After addition of trifluoroacetic acid (2 ml), the mixture was stirred for 6 days at room temperature. The solvent was removed by evaporation in vacuo, and the residue was extracted with dichloromethane. The extract was washed successively with water and saturated aqueous sodium chloride, and dried over anhydrous magnesium sulfate. Evaporation of the solvent provided a crude product, which was purified by column chromatography (chloroform/ ethanol = 50/1 (v/v)) and recrystalization (ethanol-chloroform) to give the title compound. Yield: 240 mg (55%), m.p. 262° C.

IR (KBr) (cm$^{-1}$): 1670, 1510, 1450, 1375, 1280, 240, 1175.

NMR (CDCl$_3$)δ(ppm): 7.62 (s, 1 H), 7.2–7.5 (m, 5 H), 7.16 (d, 2 H, 9 Hz), 7.02 (d, 2 H, 9 Hz), 5.11 (s, 2 H), 3.4–3.6 (m, 1 H), 2.0–2.3 (m, 2 H), 1.91 (s, 3 H), 1.5–1.8 (m, 6 H), 1.0–1.3 (m, 2 H).

EXAMPLE 8

1-cyclohexyl-5-(4'-decyloxyphenyl)-4-methyl-4-imidazolin-2-one (Compound No. 122)

2-Amino-4'-decyloxypropiophenone hydrochloride (500 mg, 1.46 mmol) was suspended in acetone (180 ml) under ice-cooling, and cyclohexyl isocyanate (201 mg, 1.61 mmol) was added thereto. Triethylamine (590 mg, 5.84 mmol) was added, and the mixture was stirred for one hour under ice-cooling. After addition of trifluoroacetic acid (2 ml), the mixture was stirred overnight at room temperature. The solvent was removed by evaporation in vacuo, and the residue was extracted with ethyl ether. The extract was washed successively with water and saturated aqueous sodium chloride, and dried over anhydrous magnesium sulfate. Evaporation of the solvent provided a crude product, which was then purified by column chromatography (chloroform/ethanol = 50/1 (v/v)) to give the title compound. Yield: 235 mg (39%), m.p. 137°–138° C.

IR (KBr) (cm$^{-1}$): 1670, 1520, 1375, 1285, 1250, 1180.

NMR (CDCl$_3$)δ(ppm): 7.18 (d, 2 H, 9 Hz), 6.95 (d, 2 H, 9 Hz), 3.96 (t, 2 H, 7 Hz), 3.13 (s, 3 H), 2.05 (s, 3 H), 1.81 (quintet, 2 H, 7 Hz), 1.2–1.6 (m, 14 H), 0.88 (t, 3 H, 7 Hz).

PREPARATION 3

4'-n-Hexyl-2-N-methoxycarbonylaminopropiophenone

2-Amino-4'-n-hexylpropiophenone hydrochloride (815 mg, 3.02 mmol) was suspended in acetone (10 ml), and methyl chloroformate (0.55 ml, 7.25 mmol) was added thereto. After addition of triethylamine (0.84 ml, 6.04 mmol), the mixture was allowed to warm to room temperature and stirred for 3 hours. The acetone was removed by evaporation, water was added to the residue, and the aqueous mixture was extracted with ethyl ether. The ether extract was dried over anhydrous magnesium sulfate and evaporated in vacuo to remove the solvent, affording the title compound. Yield: 858 mg.

EXAMPLE 9

1,4-Dimethyl-5-(4'-n-hexylphenyl)-4-imidazolin-2-one (Compound No. 1)

4'-n-Hexyl-2-N-methoxycarbonylaminopropiophenone (858 mg) and methylamine hydrochloride (992 mg, 14.7 mmol) were dissolved in dimethylformamide (2 ml), and stirred for 10 hours at 170° C. After addition of water, the mixture was extracted with ethyl acetate, and dried over anhydrous magnesium sulfate. Evaporation of the solvent in vacuo provided a crude product, which was then purified by silica gel chromatography to give the title compound. Yield: 45 mg (6%), m.p., 122°–123° C.

IR (KBr) (cm$^{-1}$) 1680, 1517, 1440, 1390.

NMR (CDCl$_3$)δ(ppm): 7.27 (d, 2 H, 8 Hz), 7.17 (d, 2 H, 8 Hz), 3.16 (s, 3 H), 2.64 (t, 2 H, 8 Hz), 2.08 (s, 3 H), 1.6–1.8 (m, 2 H), 1.2–1.5 (m, 6 H), 0.8–1.0 (m, 3 H).

PREPARATION 4

4'-n-Butyl-2-cyclohexylaminopropiophenone hydrochloride

2-Bromo-4'-n-butylpropiophenone (2713 mg, 10.1 mmol) and cyclohexylamine (3999 mg, 40.3 mmol) were dissolved in tetrahydrofuran (40 ml), and the solution was heated under reflux for 2.5 hours. The solvent was removed by evaporation in vacuo and 10% hydrochloride was added to the residue. The resultant precipitates were washed with ethyl ether and dried under vacuum, affording the title compound. Yield: 1777 mg (54%).

NMR (CDCl$_3$)δ(ppm): 7.90 (d, 2 H, 8 Hz), 7.36 (d, 2 H, 8 Hz), 4.9–5.1 (m, 1 H), 2.9–3.2 (m, 1 H), 2.70 (t, 2 H, 8 Hz), 2.0–2.3 (m, 2 H), 1.90 (d, 3 H, 7 Hz), 1.5–2.0 (m, 8 H), 1.0–1.4 (m, 4 H), 0.94 (t, 3 H, 7 Hz).

EXAMPLE 10

4-(4'-n-Butylphenyl)-1-cyclohexyl-5-methyl-4-imidazolin-2-one (Compound No. 205)

4'-n-Butyl-2-cyclohexylaminopropiophenone hydrochloride (1768 mg, 5.5 mmol) was suspended in water (30 ml), and potassium cyanate (914 mg, 11.3 mmol) in water (10 ml) was added thereto. The aqueous mixture was heated under reflux for one hour under nitrogen atomosphere, added with conc. hydrochloride (2 ml), and heated under reflux an additional one hour. The reaction mixture was extracted with dichloromethane, and the extract was washed with 10% hydrochloride, and dried over anhydrous magnesium sulfate. Evaporation of the solvent under vacuum and recrystalization from ethyl acetate gave the title compound. Yield: 155 mg (9%), m.p. 236° C.

IR (KBr) (cm$^{-1}$): 1670, 1520, 1450, 1410, 1385, 1365.

NMR (CDCl$_3$)δ(ppm): 7.64 (s, 1 H), 7.2–7.3 (m, 4 H), 3.8–4.0 (m, 1 H), 2.62 (t, 2 H, 8 Hz), 2.23 (s, 3 H), 2.1–2.3 (m, 2 H), 1.7–2.0 (m, 6 H), 1.5–1.7 (m, 2 H), 1.2–1.5 (m, 4 H), 0.93 (t, 3 H, 7 Hz).

EXAMPLE 11

5'-(4'-Cyclohexylphenyl)-1,4-dimethyl-2-hydroxyimidazole sodium salt (Compound No. 217)

5-(4'-Cyclohexylphenyl)-1,4-dimethyl-4-imidazolin-2-one (540 mg, 2.0 mmol) was dissolved in dioxane (30 ml), and sodium hydroxide (80 mg, 2.0 mmol) in water (1 ml) was added thereto. The mixture was stirred for 1.5 hours at room temperature, and precipitated crystals were filtered, affording the title compound. Yield: 80 mg (48%), m.p. >300° C.

IR (KBr) (cm$^{-1}$): 1603, 1550, 1515, 1440, 1385, 1310.

EXAMPLE 12

1. Lipoperoxidation Inhibitory Activity of Compounds of Invention

1—1. Preparation of brain homogenate

Brain homogenate was prepared using Wistar male rats in accordance with the following procedure. The rats were anesthetized through intraperitoneal administration of 45 mg/kg i.p. of pentobarbital sodium and subjected to thoracotomy. A polyethylene tube was inserted into the aorta through the left ventricle, and fixed. Brain perfusion was conducted using ice-cooled 50 mM phosphate buffered saline (PBS), pH 7.4, through the tube, and whole brain was extracted. After removal of the cerebellum, the cerebrum was weighed while wet and homogenated by a Teflon homogenizer under ice-cooling, after addition of nine-fold by weight of PBS. The resultant homogenate was centrifuged at 4° C. (2200 r.p.m., 10 minutes), and an aliquot of the supernatant (0.3 ml) was placed in a light-resistant test tube with ground stopper and used for the following test.

1-2. Evaluation of test compounds

To the brain homogenate obtained above were added PBS (0.6 ml) and an ethanol solution (10 μl) containing a predetermined amount of a test compound. Thus, each of the ethanol solutions was prepared so that the final concentration of the compound was 0.3–100 μM. The mixture was allowed to warm for 30 minutes at 37° C. (external bath temperature). After addition of 35% aqueous perchloric acid 200 μl), the mixture was centrifuged at 4° C. (2600 r.p.m., 10 minutes). The resultant supernatant was used in the following quantitative analysis. As a blank control, similar supernatant was prepared using ethanol free of test compound.

1-3. Quantitative determination of peroxidized lipid

The supernatant obtained above was admixed with 8.1% aqueous sodium dodecylsulfate (0.2 ml), 20% acetate buffer (1.5 ml), pH 3.5, 0.67% aqueous 2-thiobarbituric acid, and distilled water. The aqueous mixture was heated in a boiling-water bath for 60 minutes and cooled rapidly. Distilled water (1.0 ml) and a mixture of pyridine and butanol (1:15) (5.0 ml) were added to the cooled mixture, and the latter was shaken for 30 seconds and centrifuged (3000 r.p.m., 10 minutes). The supernatant was used as a test sample for quantitative analysis of peroxidized lipid as mentioned below. Lipoperoxide-test reagent ® containing 5 nmol/ml of 1,1,3,3-tetraethoxypropane (Wako Junyaku K. K. Japan) (0.1 ml) was used in lieu of the brain homogenate to prepare an active control.

Peroxidized lipid contained in the above supernatant was quantitatively determined by means of Fluorometer (Model 204, Hitachi Seisakusho, excitation wave length: 515 nm, fluorescent wave length: 550 nm) following the equation shown below:

$$TBA \text{ value} = 0.5 \times \frac{f}{F} \times \frac{1.1}{0.3} \times 10 \text{ (nmol/ml)}$$

TBA value: Amount of peroxidized lipid
F: Intensity of fluorescence in active control
f: Intensity of fluorescence in test sample TBA values obtained above were compared with those obtained with the blank control mentioned in Example 12, 1-2, and lipoperoxidation inhibitory percentage (%) of compound of the invention was calculated in each concentration. IC$_{50}$ values obtained by the method of least squares are listed in Table 4.

Table 4 also lists IC$_{50}$ values for idebenone and dihydroergotoxine, both of which are known to have lipoperoxidation-inhibitory activity, and for compounds similar to the compounds of the invention having the formula (I) wherein R$^2$ is p-methoxy and R$^3$ is hydrogen (referred to as Compound A), and wherein R$^2$ and R$^3$ are hydrogen (referred to as Compound B).

TABLE 4

| Anti-lipoperoxidation Activity | |
|---|---|
| Compound No. | IC$_{50}$ (μM) |
| 1 | 9.0 |
| 2 | 10.7 |
| 3 | 13.9 |
| 5 | 7.8 |
| 6 | 5.9 |
| 7 | 21.5 |
| 8 | 10.0 |
| 9 | 8.4 |
| 10 | 8.4 |
| 11 | 19.4 |
| 12 | 7.9 |
| 13 | 13.0 |
| 14 | 43.8 |
| 16 | 6.3 |
| 17 | 20.4 |
| 18 | 5.1 |

TABLE 4-continued

Anti-lipoperoxidation Activity

| Compound No. | IC$_{50}$ ($\mu$M) |
|---|---|
| 19 | 4.5 |
| 20 | 6.6 |
| 21 | 7.3 |
| 22 | 5.7 |
| 23 | 4.0 |
| 24 | 4.8 |
| 25 | 6.9 |
| 26 | 9.7 |
| 28 | 8.1 |
| 29 | 6.7 |
| 30 | 5.9 |
| 31 | 39.4 |
| 32 | 11.3 |
| 54 | 22.6 |
| 55 | 24.5 |
| 56 | 13.9 |
| 58 | 14.5 |
| 60 | 39.1 |
| 61 | 12.9 |
| 77 | 8.3 |
| 78 | 10.7 |
| 79 | 7.2 |
| 80 | 25.5 |
| 87 | 12.0 |
| 93 | 10.9 |
| 94 | 7.2 |
| 95 | 13.8 |
| 96 | 10.9 |
| 97 | 10.6 |
| 98 | 13.7 |
| 99 | 28.9 |
| 100 | 8.7 |
| 101 | 10.3 |
| 102 | 27.0 |
| 106 | 13.9 |
| 107 | 10.4 |
| 108 | 21.5 |
| 109 | 13.0 |
| 110 | 9.0 |
| 111 | 13.9 |
| 112 | 9.1 |
| 113 | 27.1 |
| 114 | 8.5 |
| 115 | 11.6 |
| 116 | 8.5 |
| 117 | 11.2 |
| 118 | 52.4 |
| 120 | 10.1 |
| 121 | 19.4 |
| 122 | 10.5 |
| 123 | 7.9 |
| 124 | 8.3 |
| 125 | 18.6 |
| 126 | 16.6 |
| 127 | 12.2 |
| 128 | 13.2 |
| 129 | 15.0 |
| 130 | 10.1 |
| 137 | 12.4 |
| 138 | 8.6 |
| 139 | 8.2 |
| 140 | 35.3 |
| 141 | 7.9 |
| 142 | 12.8 |
| Idebenone | 17.2 |
| Dihydroergotoxine | 31.8 $\mu$g/ml |
| Compound A | 147.0 |
| Compound B | >100 |

Table 4 shows that lipoperoxidation-inhibitory activities of the compounds of the invention are superior to those of known compounds.

EXAMPLE 13

Potency of Compounds of Invention as Radical Scavenger for $\alpha,\alpha$-diphenyl-$\beta$-picrylhydrazyl (DPPH)

To an ethanol solution containing 100 $\mu$M DPPH was added a test compound in ethanol (final conc. 100 $\mu$M). Absorbance of the solution at OD 516.8 nm was determined twice with 120 minutes interval. Similar determination was made with an active control which contains Vitamin C (50 $\mu$M) in lieu of the test compound. Potency of the test compound as a radical scavenger was determined following the equation below:

$$\text{Potency (\%)} = \frac{c - b}{a - b} \times 100$$

Potency: residual DPPH not scavenged (%)
a. OD at 120 minutes after addition of ethanol (30 $\mu$l)
b: OD at 120 minutes after addition of excess amount of Vitamin C
c: OD at 120 minutes after addition of a test compound.

The test results are shown in Table 5 which shows high potency of test compounds as the DPPH scavenger.

TABLE 5

Potency of Test Compounds as Radical Scavenger for Stable Radical (DPPH)

| Compound No. | Potency (%) |
|---|---|
| 1 | 86.7 |
| 2 | 98.0 |
| 8 | 99.9 |
| 16 | 80.6 |
| 25 | 95.9 |
| 26 | 95.9 |
| 78 | 78.3 |
| 111 | 87.5 |
| 122 | 88.5 |
| 137 | 59.1 |

EXAMPLE 14

Memory-Improving Activity of Compound of Invention

Passive avoidance response test was conducted in mice (15 animals per group) using light-dark differential apparatus of step-down type. The apparatus consisted of a dark room made of black and rigid vinylidene chloride resin [30 cm (depth)×30 cm (width)×31 cm (height)] and a light room, as an adjacent room, made of transparent rigid vinylidene chloride resin. The floor of the light room was set 2 cm higher than the grid surface of the dark room (step down type), and there was a guillotine door between the rooms. The animals were placed in the apparatus and acclimatized before test, and latent time for moving from the light room to the dark room was determined.

The acclimatized animals subcutaneously received 120 mg/kg of cycloheximide (Sigma) dissolved in physiological saline. After 30 minutes of the administration, the animals were placed in the light room. Immediately after the movement of the animals to the dark room, electric current was applied on the grid (0.5 mA, 3 seconds), which gave the animals "aquired behavior". After 24 hours of the establishment of the aquired behavior, a test compound suspended in 1% tragacanth was administered orally to the animals, which were then returned to the light room. Control animals received only 1% tragacanth. The latent time until an individual animal started to move to the dark room was determined.

Effectiveness of a test compound was determined by comparing the latent time before administration of the test compound with the latent time after administration, and when the latter was significantly longer than the former, the compound was regarded effective as a memory-improving agent. The minimum effective doses of the compounds which were determined as effective are listed in Table 6.

TABLE 6

| Compound No. | Memory-Improving Activity Minimum Effective Dose (mg/kg p.o.) |
|---|---|
| 1 | 0.3 |
| 2 | 0.1 |
| 5 | 30 |
| 8 | 0.1 |
| 10 | 30 |
| 11 | 30 |
| 12 | 0.3 |
| 13 | 3.0 |
| 14 | 30 |
| 16 | 0.3 |
| 18 | 0.3 |
| 23 | 30 |
| 25 | 0.1 |
| 26 | 0.1 |
| 27 | 0.1 |
| 30 | 30 |
| 32 | 3.0 |
| 58 | 0.3 |
| 77 | 0.1 |
| 78 | 0.3 |
| 87 | 30 |
| 93 | 0.1 |
| 99 | 0.1 |
| 106 | 30 |
| 109 | 0.1 |
| 111 | 0.1 |
| 116 | 30 |
| 117 | 0.1 |
| 119 | 0.1 |
| 122 | 0.1 |
| 123 | 0.1 |
| 124 | 0.1 |
| 126 | 30 |
| 127 | 30 |
| 129 | 0.3 |
| 130 | 30 |
| 137 | 0.1 |

TABLE 6-continued

| Compound No. | Memory-Improving Activity Minimum Effective Dose (mg/kg p.o.) |
|---|---|
| 141 | 0.1 |
| 142 | 0.3 |

EXAMPLE 15

Acute Toxicity

Compounds of the invention suspended in 1% tragacanth was orally administered to SD rats (both male and female) and mortality ($LD_{50}$) was determined after seven-day observation. Table 7 shows $LD_{50}$ for the typical compounds of the invention.

TABLE 7

| Compound No. | $LD_{50}$ (mg/kg p.o.) |
|---|---|
| 2 | >1000 |
| 8 | >1000 |
| 16 | >1000 |
| 137 | >1000 |

EXAMPLE 16

Pharmaceutical Formulations

Examples of pharmaceutical formulation containing as an active ingredient a compound of the invention are illustrated below.

(1) Tablets

Following components are admixed and pressed to tablets by known procedures.

| Compound No. 1 | 10 mg |
|---|---|
| Crystalline cellulose | 21 mg |
| Corn starch | 33 mg |
| Lactose | 65 mg |
| Magnesium stearate | 1.3 mg |

(2) Soft Capsules

Following components are admixed, and soft capsules are charged with the resultant mixture.

| Compound No. 1 | 10 mg |
|---|---|
| Olive oil | 105 mg |
| Lecithine | 6.5 mg |

What is claimed is:

1. A compound of the formula (I) and/or formula (II):

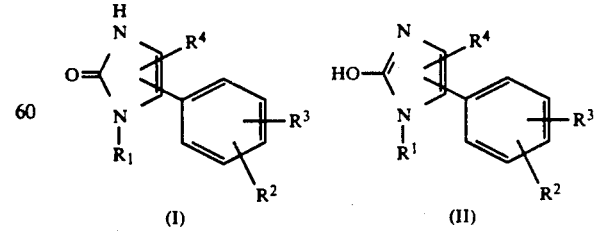

wherein
$R^1$ is $C_1$-$C_4$ alkyl, $C_5$-$C_6$ cycloalkyl, or a group of the formula:

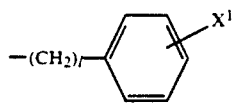

wherein $X^1$ is hydrogen, halogen, $C_1$-$C_3$ alkyl, or $C_1$-$C_3$ alkoxy, and l is an integer of 0-3;

$R^2$ represents $C_3$-$C_{20}$ alkyl, $C_3$-$C_{20}$ alkoxy, $C_5$-$C_6$ cycloalkyl, $C_1$-$C_5$ alkylthio, phenyl, or a group of the formula:

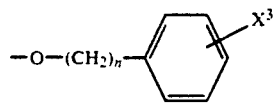

wherein $X^3$ is hydrogen, halogen, $C_1$-$C_3$ alkyl, or $C_1$-$C_3$ alkoxy, and n is an integer of 0-3;

$R^3$ represents hydrogen, $R^4$ represents $C_1$-$C_4$ alkyl, $C_5$-$C_6$ cycloalkyl, or a group of the formula:

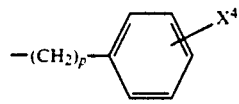

wherein $X^4$ is hydrogen, halogen, $C_1$-$C_3$ alkyl, or $C_1$-$C_3$ alkoxy, and p is an integer of 1-3, or a pharmaceutically acceptable salt thereof.

2. A compound as claimed in claim 1 wherein $R^4$ is located at the 4-position.

3. A compound as claimed in claim 1 wherein $R^2$ is located at the para-position.

4. A compound as claimed in claim 2 wherein $R^2$ is located at the para-position.

5. A lipo-peroxidation inhibitor which comprises as an essential component an effective amount of a compound of the formula (I) and/or formula (II):

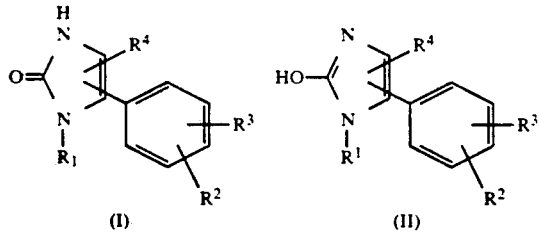

(I)  (II)

wherein $R^1$ represents $C_1$-$C_8$ alkyl, $C_3$-$C_8$ alkyl, $C_3$-$C_8$ alkynyl, $C_3$-$C_8$ cycloalkyl, or a group of the formula:

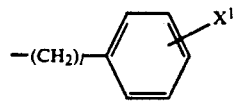

wherein $X^1$ is hydrogen, halogen, $C_1$-$C_3$ alkyl, or $C_1$-$C_3$ alkoxy, and l is an integer of 0-3;

$R^2$ and $R^3$ independently represent hydrogen, $C_3$-$C_{20}$ alkyl, $C_3$-$C_{20}$ alkenyl, $C_3$-$C_{20}$ alkynyl, $C_3$-$C_{20}$ alkoxy, $C_3$-$C_{20}$ alkenyloxy, $C_3$-$C_{20}$ alkynyloxy, $C_3$-$C_8$ cycloalkyl, $C_1$-$C_{10}$ alkylthio, a group of the formula:

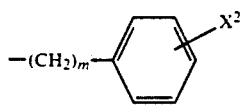

wherein $X^2$ is hydrogen, halogen, $C_1$-$C_3$ alkyl, or $C_1$-$C_3$ alkoxy, and m is an integer of 0-3, or a group of the formula:

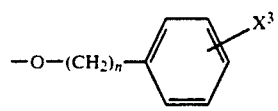

wherein $X^3$ is hydrogen, halogen, $C_1$-$C_3$ alkyl, or $C_1$-$C_3$ alkoxy, and n is an integer of 0-3;

$R^4$ represents $C_1$-$C_6$ alkyl, $C_3$-$C_8$ cycloalkyl, or a group of the formula:

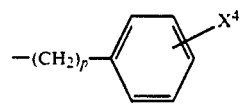

wherein $X^4$ is hydrogen, halogen, $C_1$-$C_3$ alkyl, or $C_1$-$C_3$ alkoxy, and p is an integer of 1-3;

provided that $R^2$ and $R^3$ cannot be hydrogen at the same time, or a pharmaceutically acceptable salt thereof together with a pharmaceutically acceptable excipient or carrier.

6. A radical scavenger which comprises as an essential component an effective amount of a compound

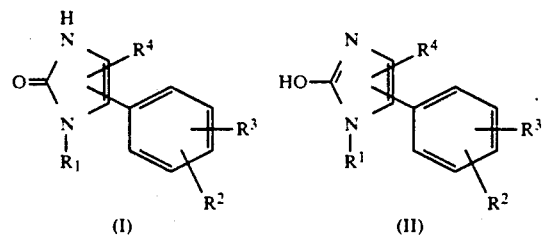

(I)  (II)

wherein $R^1$ represents $C_1$-$C_8$ alkyl, $C_3$-$C_8$ alkenyl, $C_3$-$C_8$ alkynyl, $C_3$-$C_8$ cycloalkyl, or a group of the formula:

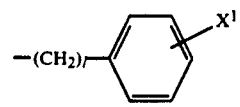

wherein $X^1$ is hydrogen, halogen, $C_1$-$C_3$ alkyl, or $C_1$-$C_3$ alkoxy, and l is an integer of 0-3;

$R^2$ and $R^3$ independently represent hydrogen, $C_3$-$C_{20}$ alkyl, $C_3$-$C_{20}$ alkenyl, $C_3$-$C_{20}$ alkynyl, $C_3$-$C_{20}$ alkoxy, $C_3$-$C_{20}$ alkenyloxy, $C_3$-$C_{20}$ alkynyloxy, $C_3$-$C_8$ cycloalkyl, $C_1$-$C_{10}$ alkylthio, a group of the formula:

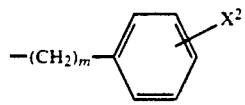

wherein $X^2$ is hydrogen, halogen, $C_1$-$C_3$ alkyl, or $C_1$-$C_3$ alkoxy, and m is an integer of 0-3, or a group of the formula:

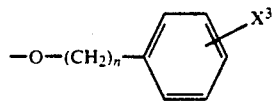

wherein $X^3$ is hydrogen, halogen, $C_1$-$C_3$ alkyl, or $C_1$-$C_3$ alkoxy, and n is an integer of 0-3;
$R^4$ represents $C_1$-$C_6$ alkyl, $C_3$-$C_8$ cycloalkyl, or a group of the formula:

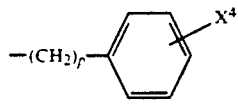

wherein $X^4$ is hydrogen, halogen, $C_1$-$C_3$ alkyl, or $C_1$-$C_3$ alkoxy, and p is an integer of 1-3;
provided that $R^2$ and $R^3$ cannot be hydrogen at the same time, or a pharmaceutically acceptable salt thereof together with a pharmaceutically acceptable excipient or carrier.

7. A memory improving agent which comprises as an essential component an effective amount of a compound

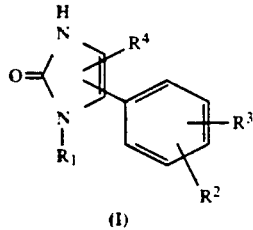 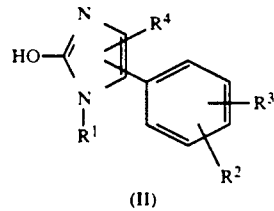

(I)   (II)

wherein $R^1$ represents $C_1$-$C_8$ alkyl, $C_3$-$C_8$ alkenyl, $C_3$-$C_8$ alkynyl, $C_3$-$C_8$ cycloalkyl, or a group of the formula:

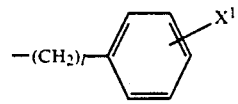

wherein $X^1$ is hydrogen, halogen, $C_1$-$C_3$ alkyl, or $C_1$-$C_3$ alkoxy, and 1 is an integer of 0-3;
$R^2$ and $R^3$ independently represent hydrogen, $C_3$-$C_{20}$ alkyl, $C_3$-$C_{20}$ alkenyl, $C_3$-$C_{20}$ alkynyl, $C_3$-$C_{20}$ alkoxy, $C_3$-$C_{20}$ alkenyloxy, $C_3$-$C_{20}$ alkynyloxy, $C_3$-$C_8$ cycloalkyl, $C_1$-$C_{10}$ alkylthio, a group of the formula:

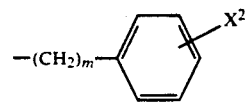

wherein $X^2$ is hydrogen, halogen, $C_1$-$C_3$ alkyl, or $C_1$-$C_3$ alkoxy, and m is an integer of 0-3, or a group of the formula:

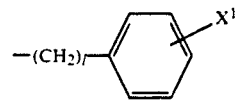

wherein $X^3$ is hydrogen, halogen, $C_1$-$C_3$ alkyl, or $C_1$-$C_3$ alkoxy, and n is an integer of 0-3;
$R^4$ represents $C_1$-$C_6$ alkyl, $C_3$-$C_8$ cycloalkyl, or a group of the formula:

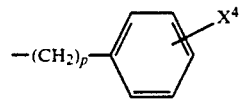

wherein $X^4$ is hydrogen, halogen, $C_1$-$C_3$ alkyl, or $C_1$-$C_3$ alkoxy, and p is an integer of 1-3;
provided that $R^2$ and $R^3$ cannot be hydrogen at the same time, or a pharmaceutically acceptable salt thereof together with a pharmaceutically acceptable excipient or carrier.

* * * * *